(12) United States Patent
Lu et al.

(10) Patent No.: US 8,211,901 B2
(45) Date of Patent: Jul. 3, 2012

(54) NAPHTHAMIDE DERIVATIVES AS MULTI-TARGET PROTEIN KINASE INHIBITORS AND HISTONE DEACETYLASE INHIBITORS

(75) Inventors: Xian-Ping Lu, Belle Meade, NJ (US); Zhibin Li, Shenzhen (CN); Song Shan, Shenzhen (CN); Jindi Yu, Shenzhen (CN); Zhiqiang Ning, Shenzhen (CN)

(73) Assignee: Shenzhen Chipscreen Biosciences Ltd., Shenzhen (CN)

( * ) Notice: Subject to any disclaimer, the term of this patent is extended or adjusted under 35 U.S.C. 154(b) by 173 days.

(21) Appl. No.: 12/785,111

(22) Filed: May 21, 2010

(65) Prior Publication Data

US 2010/0298358 A1  Nov. 25, 2010

Related U.S. Application Data

(60) Provisional application No. 61/180,497, filed on May 22, 2009.

(51) Int. Cl.
*A61K 31/517* (2006.01)
*A61K 31/47* (2006.01)

(52) U.S. Cl. .................. 514/266.3; 514/312; 544/287; 546/153

(58) Field of Classification Search ............... 544/287; 546/153
See application file for complete search history.

(56) References Cited

U.S. PATENT DOCUMENTS

| | | | |
|---|---|---|---|
| 7,041,687 B2 | 5/2006 | Binch et al. | |
| 7,098,330 B2 | 8/2006 | Bebbington et al. | |
| 7,115,739 B2 | 10/2006 | Bebbington et al. | |
| 7,125,905 B2 | 10/2006 | Tang et al. | |
| 7,132,533 B2 | 11/2006 | Benedict et al. | |
| 7,151,096 B2 | 12/2006 | Ren et al. | |
| 7,157,476 B2 | 1/2007 | Come et al. | |
| 7,166,597 B2 | 1/2007 | Alberti et al. | |
| 7,179,910 B2 | 2/2007 | Guan et al. | |
| 7,189,721 B2 | 3/2007 | Tang et al. | |
| 7,214,700 B2 | 5/2007 | Wei et al. | |
| 2002/0103192 A1 | 8/2002 | Curtin et al. | |

FOREIGN PATENT DOCUMENTS

| | | |
|---|---|---|
| EP | 0847992 A1 | 6/1998 |
| WO | WO0118171 A2 | 3/2001 |
| WO | WO0170675 A2 | 9/2001 |
| WO | WO0226696 A1 | 4/2002 |

OTHER PUBLICATIONS

Tan, S-L. et al., "Resistance to Experimental Autoimmune Encephalomyelitis and Impaired IL-17 Production in Protein Kinase C$\theta$-Deficient Mice", The Journal of Immunology, 2006, vol. 176, pp. 2872-2879.

Healy, A. M., et al., "PKC-$\delta$-Deficient Mice Are Protected from Th1-Dependent Antigen-Induced Arthritis", The Journal of Immunology, 2006, vol. 177, pp. 1886-1893.

Salek-Ardakani, S. et al., "Protein Kinase C$\theta$ Controls Th1 Cells in Experimental Autoimmune Encephalomyelitis", The Journal of Immunology, 2005, vol. 175, pp. 7635-7641.

Kim, J. et al., "PKC-$\theta$ Knockout Mice are Protected from Fat-induced Insulin Resistance", The Journal of Clinical Investigation, 2004, vol. 114, No. 6, 823-827.

Wikstrand, C. L. et al., "Prognostic Applications of the Epidermal Growth Factor Receptor and its Ligand, Transforming Growth Factor-$\alpha$", Journal of the National Cancer Institute, 1998, vol. 90, No. 11, pp. 799-801.

Mendelsohn, J., "Epidermal Growth Factor Receptor Inhibition by a Monoclonal Antibody as Anticancer Therapy", Clinical Cancer Research, 1997, vol. 3, pp. 2703-2707.

Haq, S. et al., "Glycogen Synthase Kinase-3$\beta$ is a Negative Regulator of Cardiomyocyte Hypertrophy", The Journal of Cell Biology, 2000, vol. 151, No. 1, pp. 117-129.

Schumacher, J. M. et al., "AIR-2: An Aurora/Ipl1-related Protein Kinase Associated with Chromosomes and Midbody Microtubules is Required for Polar Body Extrusion and Cytokinesis in *Caenorhabditis elegans* Embryos", The Journal of Cell Biology, 1998, vol. 143, No. 6, pp. 1635-1646.

Kimura, M. et al., "Cell Cycle-dependent Expression and Spindle Pole Localization of a Novel Human Protein Kinase, Aik, Related to Aurora of *Drosophila* and Yeast Ipl1", The Journal of Biological Chemistry, 1997, vol. 272, No. 21, pp. 13766-13771.

(Continued)

*Primary Examiner* — James O Wilson
*Assistant Examiner* — Brian McDowell
(74) *Attorney, Agent, or Firm* — Eckert Seamans Cherin & Mellott, LLC

(57) ABSTRACT

Isolated compounds of formula I:

and stereoisomers, enantiomers, diastereomers, and pharmaceutically acceptable salts thereof are described, as well as processes for production, and methods of use of these compounds and compositions thereof for the treatment of diseases associated with abnormal protein kinase activities and/or abnormal histone deacetylase activities including, for example, inflammatory diseases, autoimmune diseases, cancer, neurological and neurodegenerative diseases, cardiovascular diseases, metabolic disease, allergies and asthma and/or hormone-related diseases.

18 Claims, 3 Drawing Sheets

OTHER PUBLICATIONS de Ruijter, A. J. M., et al, "Histone Deacetylases (HDACs): Characterization of the Classical HDAC Family", Biochemical Journal, 2003, vol. 370, pp. 737-749.

Marks, P-A., et al., "Histone Deacetylases and Cancer: Causes and Therapies", Nature Reviews Cancer, 2001, vol. 1, pp. 194-202.

Dokmanovic, M. et al. "Prospects: Histone Deacetylase Inhibitors", Journal of Cellular Biochemistry, 2005, vol. 96, pp. 293-304.

Lagger, G. et al., "Essential Function of Histone Deacetylase 1 in Proliferation Control and CDK Inhibitor Repression", The EMBO Journal, 2002, vol. 21, No. 11, pp. 2672-2681.

Bartl, S. et al., "Identification of Mouse Histone Deacetylase 1 as a Growth Factor-Inducible Gene", Molecular and Cellular Biology, 1997, vol. 17, No. 9, pp. 5033-5043.

Wilson, A-J. et al., "Histone Deacetylase 3(HDAC3) and Other Class I HDACs Regulate Colon Cell Maturation and p21 Expression and Are Deregulated in Human Colon Cancer", The Journal of Biological Chemistry, 2006, vol. 281, No. 19, pp. 13548-13558.

Sakuma, T. et al., "Aberrant Expression of Histone Deacetylase 6 in Oral Squamous Cell Carcinoma", International Journal of Oncology, 2006, vol. 29, pp. 117-124.

Herman, D. et al., "Histone Deacetylase Inhibitors Reverse Gene Silencing in Friedreich's Ataxia", Nature Chemical Biology, 2006, vol. 2, No. 10, pp. 551-559.

Avila, A. M. et al., "Trichostatin A Increases SMN Expression and Survival in a Mouse Model of Spinal Muscular Atrophy", The Journal of Clinical Investigation, 2007, vol. 117, No. 3, pp. 659-671.

Gialitakis, M. et al., "Coordinated Changes of Histone Modifications and HDAC Mobilization Regulate the Induction of MHC Class II Genes by Trichostatin A", Nucleic Acids Research, 2006, vol. 34, No. 3, pp. 765-772.

Arteaga, C. L. et al, "Tyrosine Kinase Inhibitors-ZD1839 (Iressa)", Current Opinion in Oncology, (2001), vol. 13, No. 6, pp. 491-498.

Viloria Petit, A-M. et al., "Neutralizing Antibodies against Epidermal Growth Factor and ErbB-2/neu Receptor Tyrosine Kinases Down-Regulate Vascular Endothelial Growth Factor Production by Tumor Cells in Vitro and in Vivo", American Journal of Pathology, (1997), vol. 5, No. 6, pp. 1523-1530.

Rarikh, A. A. et al., "The Vascular Endothelial Growth Factor Family and its Receptors", Hematology/Oncology Clinics of North America, (2004), vol. 18, pp. 951-971.

Monia, et al., "Antitumor Activity of a Phosphorothioate Antisense Oligodeoxynucleotide Targeted Against C-raf Kinase", Nature Medicine, (1996), vol. 2, No. 6, pp. 668-675.

Grunstein, M., "Histone Acetylation in Chromatin Structure and Transcription", Nature, (1997), vol. 389, pp. 349-352.

Grignani, F. et al., "Fusion Proteins of the Retinoic Acid Receptor-α Recruit Histone Deacetylase in Promyelocytic Leukaemia", Nature, (1998), vol. 391, pp. 815-818.

Lin, R. J. et al., "Role of the Histone Deacetylase Complex in Acute Promyelocytic Leukaemia", Nature, (1998), vol. 391, pp. 811-814.

Glaser, K. B. et al., "Role of Class I and Class II Histone Deacetylases in Carcinoma Cells Using siRNA", Biochemical and Biophysical Research Communications, (2003), vol. 310, No. 2, pp. 529-536.

Trivedi, C. M. et al., "Hdac2 Regulates the Cardiac Hypertrophic Response by Modulating Gsk3β Activity", Nature Medicine, (2007), vol. 13, No. 3, pp. 324-331.

Glaros, S. et al., "The Reversible Epigenetic Silencing of BRM: Implications for Clinical Targeted Therapy", Oncogene, (2007), vol. 26, pp. 7058-7066.

Mai, A. et al., "Novel Pyrrole-Containing Histone Deacetylase Inhibitors Endowed with Cytodifferentiation Activity", The International Journal of Biochemistry & Cell Biology, (2007), vol. 39, pp. 1510-1522.

Vincent, A. et al., "Epigenetic Regulation(DNA Methylation, Histone Modifications) of the 11p15 Mucin Genes (MUC2, MUC5AC, MUC5AC, MUC5B, MUC6) in Epithelial Cancer Cells", Oncogene, (2007), vol. 26, pp. 6566-6576.

De Bore, J. et al., "Inhibition of Histone Acetylation as a Tool in Bone Tissue Engineering", Tissue Engineering, (2006), vol. 12, No. 10, pp. 2927-2937.

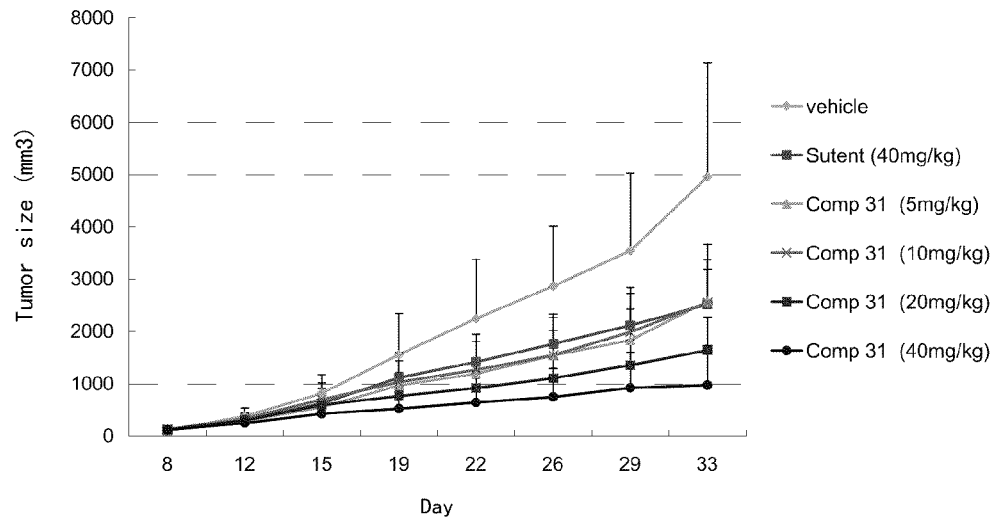
Figure 1. Antitumor activity upon treatment with compound 31 in human A549 lung cancer xenograft model.
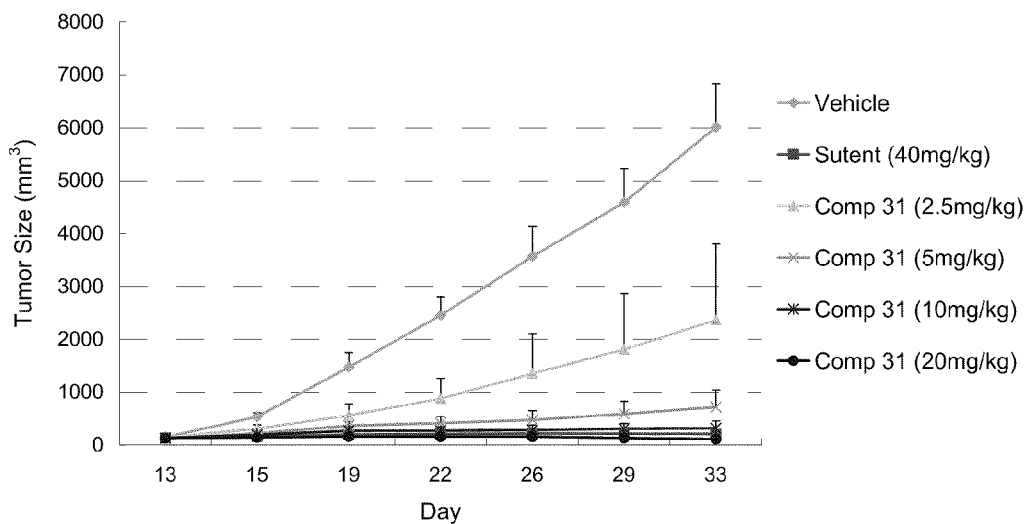
Figure 2. Antitumor activity upon treatment with compound 31 in human HCT-8 colon cancer xenograft model.

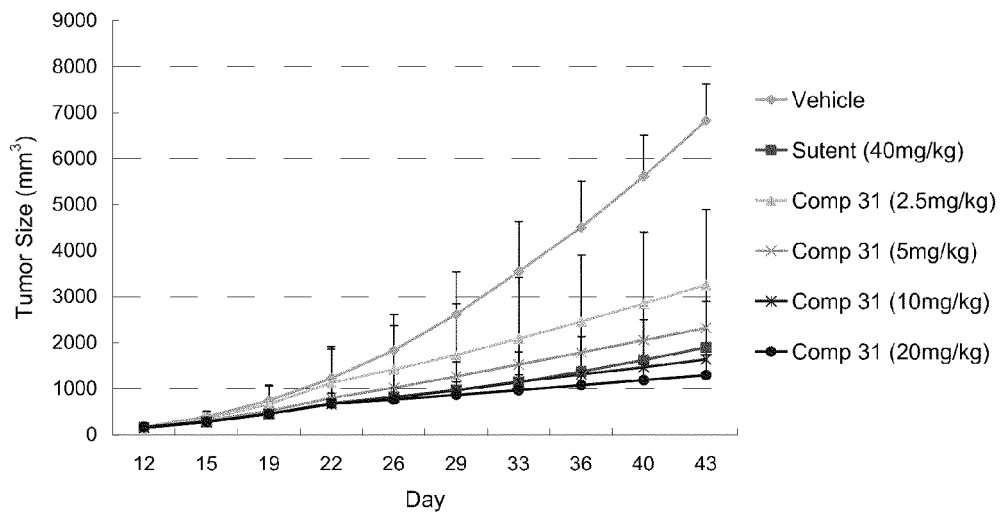
Figure 3. Antitumor activity upon treatment with compound 31 in human SSMC7721 liver cancer xenograft model.
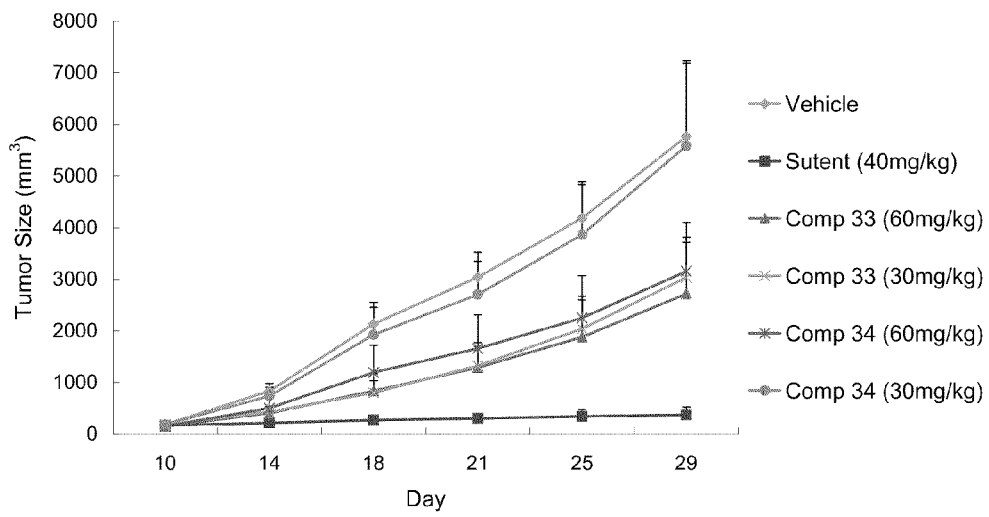
Figure 4. Antitumor activity upon treatment with compound 33 and compound 34 in human HCT-8 colon cancer xenograft model.

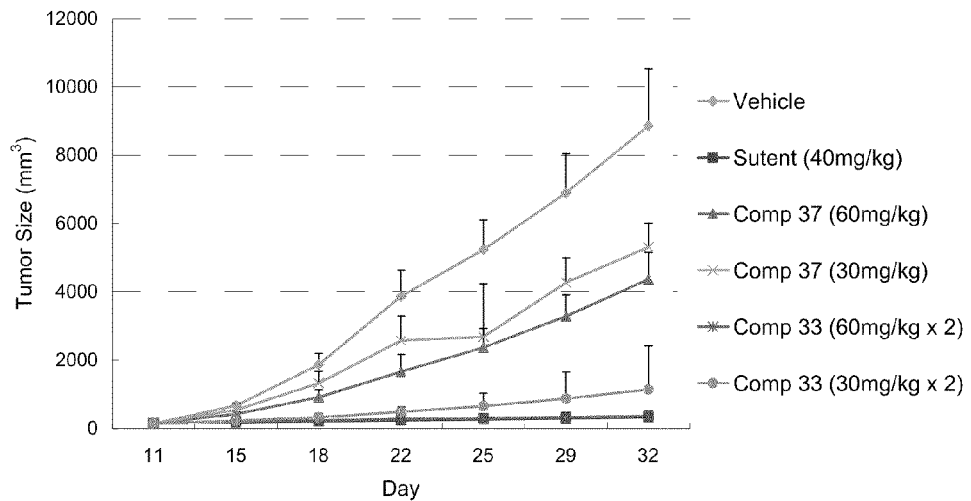
Figure 5. Antitumor activity upon treatment with compound 33 and compound 37 in human HCT-8 colon cancer xenograft model.
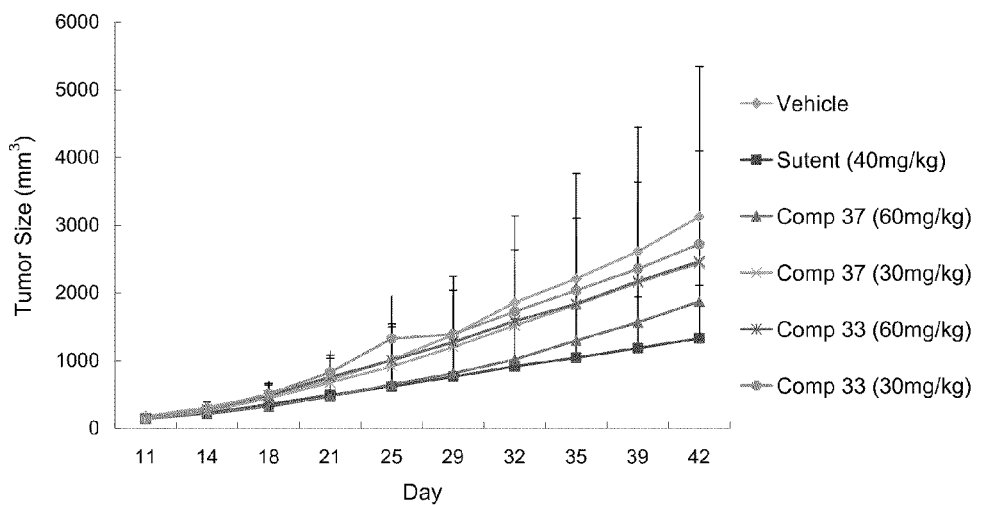
Figure 6. Antitumor activity upon treatment with compound 33 and compound 37 in human SSMC7721 liver cancer xenograft model.

NAPHTHAMIDE DERIVATIVES AS MULTI-TARGET PROTEIN KINASE INHIBITORS AND HISTONE DEACETYLASE INHIBITORS

CROSS REFERENCE TO RELATED APPLICATIONS

This application claims the benefit of U.S. Provisional Application No. 61/180,497, filed May 22, 2009, which is incorporated herein by reference.

FIELD OF INVENTION

The present invention relates to naphthamide derivatives which are capable of inhibiting protein kinases and histone deacetylases. The compounds of this invention are therefore useful in treating diseases associated with abnormal protein kinase activities or abnormal histone deacetylase activities. Pharmaceutical compositions comprising these compounds, methods of treating diseases utilizing pharmaceutical compositions comprising these compounds, and methods of preparing these compounds are also disclosed.

BACKGROUND OF THE INVENTION

Protein kinases are a family of enzymes that catalyze the phosphorylation of proteins, in particular the hydroxy group of specific tyrosine, serine and threonine residues in proteins. Protein kinases play a critical role in the regulation of a wide variety of cellular processes, including metabolism, cell proliferation, cell differentiation, cell survival, environment-host reaction, immune response, and angiogenesis. Many diseases are associated with abnormal cellular responses triggered by protein kinase-mediated events. These diseases include inflammatory diseases, autoimmune diseases, cancer, neurological and neurodegenerative diseases, cardiovascular diseases, allergies and asthma or hormone-related disease (Tan, S-L., 2006, *J. Immunol.*, 176: 2872-2879; Healy, A. ea al., 2006, *J. Immunol.*, 177: 1886-1893; Salek-Ardakani, S. et al., 2005, *J. Immunol.*, 175: 7635-7641; Kim, J. et al., 2004, *J. Clin. Invest.*, 114: 823-827). Therefore, considerable effort has been made to identify protein kinase inhibitors that are effective as therapeutic agents against these diseases.

The protein kinases can be conventionally divided into two classes, the protein tyrosine kinases (PTKs) and the serine-threonine kinases (STKs).

The protein tyrosine kinases (PTKs) are divided into two classes: the non-transmembrane tyrosine kinases and transmembrane growth factor receptor tyrosine kinases (RTKs). At present, at least nineteen distinct subfamilies of RTKs have been identified, such as the epidermal growth factor receptor (EGFR), the vascular endothelial growth factor receptor (VEGFR), the platelet derived growth factor receptor growth factor receptor (PDGFR), and the fibroblast growth factor receptor (FGFR).

The epidermal growth factor receptor (EGFR) family comprises four transmembrane tyrosine kinase growth factor receptors: HER1, HER2, HER3 and HER4. Binding of a specific set of ligands to the receptor promotes EGFR dimerization and results in the receptors autophosphorylation on tyrosine residues (Arteaga, C-L., 2001, *Curr. Opin. Oncol.*, 6: 491-498). Upon autophosphorylation of the receptor several signal transduction pathways downstream of EGFR become activated. The EGFR signal transduction pathways have been implicated in the regulation of various neoplastic processes, including cell cycle progression, inhibition of apoptosis, tumor cell motility, invasion and metastasis. EGFR activation also stimulates vascular endothelial growth factor (VEGF), which is the primary inducer of angiogenesis (Petit, A-M. et al., 1997, *Am. J. Pathol.*, 151: 1523-1530). In experimental models, deregulation of the EGFR-mediated signal transduction pathways is associated with oncogenesis (Wikstrand, C-J. et al., 1998, *J Natl Cancer Inst.*, 90: 799-800). Mutations leading to continuous activation of amplification and over expression of EGFR proteins are seen in many human tumors, including tumors of breast, lung, ovaries and kidney. These mutations are a determinant of tumor aggressiveness (Wikstrand, C-J. et al., 1998, *J Natl Cancer Inst.*, 90: 799-800). EGFR over expression is frequently seen in non-small cell lung cancer (NSCLC). Activity of EGFR can be inhibited either by blocking the extracellular ligand binding domain with the use of anti-EGFR antibodies or by the use of small molecules that inhibit the EGFR tyrosine kinase, thus resulting in inhibition of downstream components of the EGFR pathway (Mendelsohn, J., 1997, *Clin. Can. Res.*, 3: 2707-2707).

The vascular endothelial growth factor (VEGF) is secreted by almost all solid tumors and tumor associated stroma in response to hypoxia. It is highly specific for vascular endothelium and regulates both vascular proliferation and permeability. Excessive expression of VEGF levels correlate with increased microvascular density, cancer recurrence and decreased survival (Parikh, A-A., 2004; *Hematol. Oncol. Clin. N. Am.*, 18:951-971). There are 6 different ligands for the VEGF receptor, VEGF-A through-E and placenta growth factor. Ligands bind to specific receptors on endothelial cells, mostly VEGFR-2. The binding of VEGF-A to VEGFR-1 induces endothelial cell migration. Binding to VEGFR-2 induces endothelial cell proliferation, permeability and survival. VEGFR-3 is thought to mediate lymphangiogenesis. The binding of VEGF to VEGFR-2 receptors results in activation and autophosphorylation of intracellular tyrosine kinase domains which further triggers other intracellular signaling cascades (Parikh, A-A., 2004, *Hematol. Oncol. Clin. N. Am.*, 18:951-971).

The serine-threonine kinases (STKs) are predominantly intracellular although there are a few receptor kinases of the STK type. STKs are the most common forms of the cytosolic kinases that perform their function in the part of the cytoplasm other than the cytoplasmic organelles and cytoskelton.

Glycogen synthase kinase-3 (GSK-3) is a serine-threonine protein kinase comprised of $\alpha$ and $\beta$ isoforms that are each encoded by distinct genes. GSK-3 has been found to phosphorylate and modulate the activity of a number of regulatory proteins. GSK-3 has been implicated in various diseases including diabetes, Alzheimer's disease, CNS disorders such as manic depressive disorder and neurodegenerative diseases, and cardiomyocyte hypertrophy (Haq, et al., 2000, *J. Cell Biol.*, 151: 117).

Aurora-2 is a serine-threonine protein kinase that has been implicated in human cancer, such as colon, breast, and other solid tumors. This kinase is believed to be involved in protein phosphorylation events that regulate cell cycle. Specifically, Aurora-2 may play a role in controlling the accurate segregation of chromosomes during mitosis. Misregulation of the cell cycle can lead to cellular proliferation and other abnormalities. In human colon cancer tissue, the Aurora-2 protein has been found to be over expressed (Schumacher, et al., 1998, *J. Cell Biol.*, 143: 1635-1646; Kimura et al., 1997, *J. Biol. Chem.*, 272: 13766-13771).

The cyclin-dependent kinases (CDKs) are serine-threonine protein kinase that regulates mammalian cell division. CDKs play a key role in regulating cell machinery. To date, nine kinase subunits (CDK 1-9) have been identified. Each kinase associates with a specific regulatory partner and together makes up the active catalytic moiety. Uncontrolled proliferation is a hallmark of cancer cells, and misregulation of CDK function occurs with high frequency in many important solid tumors. CDK2 and CDK4 are of particular interest because their activities are frequently misregulated in a wide variety of human cancers.

Raf kinase, a downstream effector of ras oncoprotein, is a key mediator of signal-transduction pathways from cell surface to the cell nucleus. Inhibition of raf kinase has been correlated in vitro and in vivo with inhibition of the growth of variety of human tumor types (Monia et al., 1996, *Nat. Med.,* 2: 668-675).

Other serine-threonine protein kinases include the protein kinase A, B and C. These kinases, known as PKA, PKB and PKC, play key roles in signal transduction pathways.

Many attempts have been made to identify small molecules which act as protein kinase inhibitors useful in the treatment of diseases associated with abnormal protein kinase activities. For example, cyclic compounds (U.S. Pat. No. 7,151, 096), bicyclic compounds (U.S. Pat. No. 7,189,721), tricyclic compounds (U.S. Pat. No. 7,132,533), (2-oxindol-3-ylidenyl)acetic acid derivatives (U.S. Pat. No. 7,214,700), 3-(4-amidopyrrol-2-ylmethlidene)-2-indolinone derivatives (U.S. Pat. No. 7,179,910), fused pyrazole derivatives (U.S. Pat. No. 7,166,597), aminofurazan compounds (U.S. Pat. No. 7,157, 476), pyrrole substituted 2-indolinone compounds (U.S. Pat. No. 7,125,905), triazole compounds (U.S. Pat. No. 7,115, 739), pyrazolylamine substituted quinazoline compounds (U.S. Pat. No. 7,098,330) and indazole compounds (U.S. Pat. No. 7,041,687) have all been described as protein kinase inhibitors. Several protein kinase inhibitors such as Glivec, Suten, and Sorafenib have been successfully approved by FDA as anti-cancer therapy. Their clinic uses demonstrated clear advantages over existing chemotherapeutical treatments, fueling continuing interests in innovation of mechanism-based treatments and improvement of chemical scaffolds to discover new compounds with excellent oral bioavailability, significant anti-tumor activity, and lower toxicity at well-tolerated dose.

SUMMARY OF THE INVENTION

The present invention is directed to certain naphthamide derivatives which are capable of selectively inhibiting protein kinases and histone deacetylases and are therefore useful in treating diseases associated with abnormal protein kinase activities and abnormal histone deacetylase activities. In particular, they are highly effective against hematological malignancy and solid carcinomas.

BRIEF DESCRIPTION OF THE FIGURES

FIG. 1 graphically illustrates the antitumor activity of compound 31 in human A549 lung cancer xenograft model.

FIG. 2 graphically illustrates the antitumor activity of compound 31 in human HCT-8 colon cancer xenograft model.

FIG. 3 graphically illustrates the antitumor activity of compound 31 in human SSMC7721 liver cancer xenograft model.

FIG. 4 graphically illustrates the antitumor activity of compound 33 and compound 34 in human HCT-8 colon cancer xenograft model.

FIG. 5 graphically illustrates the antitumor activity of compound 33 and compound 37 in human HCT-8 colon cancer xenograft model.

FIG. 6 graphically illustrates the antitumor activity of compound 33 and compound 37 in human SSMC7721 liver cancer xenograft model.

DETAILED DESCRIPTION OF THE INVENTION

Various publications are cited throughout the present application. The contents of these publications and contents of documents cited in these publications are incorporated herein by reference.

Histone deacetylase (HDAC) proteins play a critical role in regulating gene expression in vivo by altering the accessibility of genomic DNA to transcription factors. Specifically, HDAC proteins remove the acetyl group of acetyl-lysine residues on histones, which can result in nucleosomal remodelling (Grunstein, M., 1997, *Nature,* 389: 349-352). Due to their governing role in gene expression, HDAC proteins are associated with a variety of cellular events, including cell cycle regulation, cell proliferation, differentiation, reprogramming of gene expression, and cancer development (Ruijter, A-J-M., 2003, Biochem. J., 370: 737-749; Grignani, F., 1998, Nature, 391: 815-818; Lin, R-J., 1998, 391: 811-814; Marks, P-A., 2001, Nature Reviews Cancer, 1: 194). In fact, HDAC inhibitors have been demonstrated to reduce tumor growth in various human tissues and in animal studies, including lung, stomach, breast, and prostrate (Dokmanovic, M., 2005, J. Cell Biochenm., 96: 293-304).

Mammalian HDACs can be divided into three classes according to sequence homology. Class I consists of the yeast Rpd3-like proteins (HDAC 1, 2, 3, 8 and 11). Class II consists of the yeast HDA1-like proteins (HDAC 4, 5, 6, 7, 9 and 10). Class III consists of the yeast SIR2-like proteins (SIRT 1, 2, 3, 4, 5, 6 and 7).

The activity of HDAC1 has been linked to cell proliferation, a hallmark of cancer. Particularly, mammalian cells with knock down of HDAC1 expression using siRNA were antiproliferative (Glaser, K-B., 2003, *Biochem. Biophys. Res. Comm.,* 310: 529-536). While the knock out mouse of HDAC1 was embryonic lethal, the resulting stem cells displayed altered cell growth (Lagger, G., 2002, *EMBO J.,* 21: 2672-2681). Mouse cells overexpressing HDAC1 demonstrated a lengthening of $G_2$ and M phases and reduced growth rate (Bartl. S., 1997, Mol. Cell. Biol., 17: 5033-5043). Therefore, the reported data implicate HDAC1 in cell cycle regulation and cell proliferation.

HDAC2 regulates expression of many fetal cardiac isoforms. HDAC2 deficiency or chemical inhibition of histone deacetylase prevented the re-expression of fetal genes and attenuated cardiac hypertrophy in hearts exposed to hypertrophic stimuli. Resistance to hypertrophy was associated with increased expression of the gene encoding inositol polyphosphate-5-phosphatase f (Inpp5f) resulting in constitutive activation of glycogen synthase kinase 3β (Gsk3β) via inactivation of thymoma viral proto-oncogene (Akt) and 3-phosphoinositide-dependent protein kinase-1 (Pdk1). In contrast, HDAC2 transgenic mice had augmented hypertrophy associated with inactivated Gsk3β. Chemical inhibition of activated Gsk3β allowed HDAC2-deficient adults to become sensitive to hypertrophic stimulation. These results suggest that HDAC2 is an important molecular target of HDAC inhibitors in the heart and that HDAC2 and Gsk3β are components of a regulatory pathway providing an attractive therapeutic target for the treatment of cardiac hypertrophy and heart failure (Trivedi, C-M., 2007, *Nat. Med.* 13: 324-331).

HDAC3 are maximally expressed in proliferating crypt cells in normal intestine. Silencing of HDAC3 expression in colon cancer cell lines resulted in growth inhibition, a decrease in cell survival, and increased apoptosis. Similar effects were observed for HDAC2 and, to a lesser extent, for HDAC1. HDAC3 gene silencing also selectively induced expression of alkaline phosphatase, a marker of colon cell maturation. Concurrent with its effect on cell growth, overexpression of HDAC3 inhibited basal and butyrate-induced p21 transcription in a Sp1/Sp3-dependent manner, whereas silencing of HDAC3 stimulated p21 promoter activity and expression. These findings identify HDAC3 as a gene deregulated in human colon cancer and as a novel regulator of colon cell maturation and p21 expression (Wilson, A-J., 2006, *J. Biol. Chem.*, 281: 13548-13558).

HDAC6 is a subtype of the HDAC family that deacetylates alpha-tubulin and increases cell motility. Using quantitative real-time reverse transcription polymerase chain reaction and Western blots on nine oral squamous cell carcinoma (OSCC)-derived cell lines and normal oral keratinocytes (NOKs), HDAC6 mRNA and protein expression were commonly upregulated in all cell lines compared with the NOKs. Immunofluorescence analysis detected HDAC6 protein in the cytoplasm of OSCC cell lines. Similar to OSCC cell lines, high frequencies of HDAC6 up-regulation were evident in both mRNA (74%) and protein (51%) levels of primary human OSCC tumors. Among the clinical variables analyzed, the clinical tumor stage was found to be associated with the HDAC6 expression states. The analysis indicated a significant difference in the HDAC6 expression level between the early stage (stage I and II) and advanced-stage (stage III and IV) tumors (P=0.014). These results suggest that HDAC6 expression may be correlated with tumor aggressiveness and offer clues to the planning of new treatments (Sakuma, T., 2006, *Int. J. Oncol.*, 29: 117-124).

Epigenetic silencing of functional chromosomes by HDAC is one of major mechanisms occurred in many pathological processes, in which functionally critical genes are repressed or reprogrammed by HDAC activities leading to the loss of phenotypes in terminal differentiation, maturation and growth control, and the loss of functionality of tissues. For example, tumor suppressor genes are often silenced during development of cancer and chemical inhibitor of HDAC can derepressed the expression of these tumor suppressor genes, leading to growth arrest and differentiation (Glaros S et al., 2007, Oncogene June 4 Epub ahead of print; Mai, A, et al., 2007, Int J. Biochem Cell Bio., April 4, Epub ahead of print; Vincent A. et al., 2007, Oncogene, April 30, Epub ahead of print; our unpublished results); and repression of structural genes such as FXN in Friedreich's ataxia and SMN in spinal muscular atrophy can be reversed by HDAC inhibitors that lead to re-expression of FXN and SMN genes and resume the functions in the tissues (Herman D et al., 2006, Nature Chemical Biology, 2(10):551-8; Avila A M et al., 2007, J Clinic Investigation, 117(3)659-71; de Bore J, 2006, Tissue Eng. 12(10):2927-37); Induction of entire MHC II family gene expression through reprogramming of HDAC "hot spot" in chromosome 6p21-22 by HDAC inhibitor further extend epigenetic modulation of immune recognition and immune response (Gialitakis M et al., 2007, Nucleic Acids Res., 34(1); 765-72).

Several classes of HDAC inhibitors have been identified, including (1) short-chain fatty acids, e.g. butyrate and phenylbutyrate; (2) organic hydroxamic acids, e.g. suberoylanilide hydroxamic acid (SAHA) and trichostatin A (TSA); (3) cyclic tetrapeptides containing a 2-amino-8-oxo 9,10-expoxydecanoyl (AOE) moiety, e.g. trapoxin and HC-toxin; (4) cyclic peptides without the AOE moiety, e.g. apicidin and FK228; and (5) benzamides, e.g. MS-275 (EP0847992A1, US2002/0103192A1, WO02/26696A1, WO01/70675A2, WO01/18171A2). Although, HDAC inherited very promising biological roles as a drug target especially on cancer biology side, such as preferential apoptosis-induction in malignant cells but not normal cells, differentiation of epithelia in cancer cells, anti-inflammatory and immunomodulation, and cell cycle arrest and can be consider as "neo-chemotherapy" with much improved toxicity over existing chemotherapy, the success of SAHA from Merck is currently only limited to the treatment of cutaneous T cell lymphoma whereas no major solid tumors yet been reported to be highly effective by this treatment. Therefore, there is still a need to discover new compounds with improved profiles, such as stronger HDAC inhibitory activity and anti-cancer activity, more selective inhibition on different subtype of HDAC, and lower toxicity.

The favorite metaphor for cancer drug developers has long been the target therapy. One hoped to design a drug that could hit tumor cells in one specific target, knocking out tumor cells while leaving normal cells undamaged. Cancer cells, however, can use multiple biological triggers and pathways to grow and spread throughout the body. Hitting them in one target will also render them to regroup and redeploy along new growth paths. That realization has led to the development of combination target therapies, which are becoming the new paradigm for cancer treatment. Several multi-target kinase inhibitors are now in development, two, Sorafenib and Suten, are already approved in the United States. For example, Sorafenib, developed by Bayer Pharmaceuticals, is the first drug targeting both the RAF/MEK/ERK pathway (involved in cell proliferation) and the VEGFR2/PDGFRβ signaling cascade (involved in angiogenesis). This drug was first approved in December 2005 for advanced kidney cancer, a disease that is believed to be highly dependent on angiogenesis. However, these target therapies, although are effective against some solid tumors, but far from satisfaction in terms of reaching a better efficacy as a single agent against other solid tumors while tolerable side-effects associated with treatment can be maintained.

PROVIDED HEREIN are new chemical compounds that combine anti-angiogenesis and anti-proliferation activities of RTK's together with differentiation-inducing, immune modulation, cell cycle arrest and apoptosis-induction activities of more selective HDACi, to reach a better efficacy against solid tumors while overcoming side effects such as hypertension, QT prolongation, thyroid gland regression, skin rash and discoloration, and pains associated with currently marketed RTK inhibitors.

Particularly, the present invention provides a compound having the structure represented by formula (I), or its stereoisomer, enantiomer, diastereomer, hydrate, or pharmaceutically acceptable salts thereof:

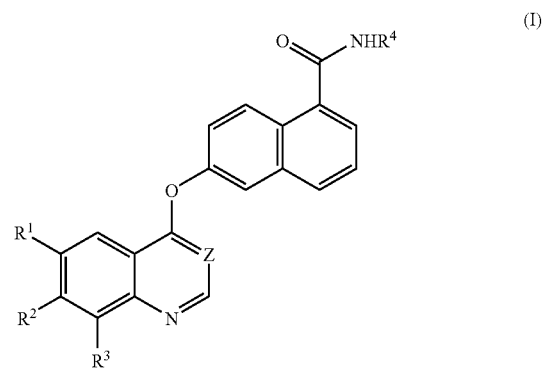

wherein
  Z is CH or N;
  $R^1$, $R^2$ and $R^3$ are independently hydrogen, halo, alkyl, alkoxy or trifluoromethyl;
  $R^4$ is

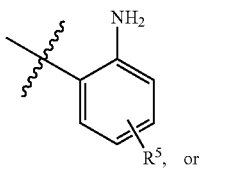

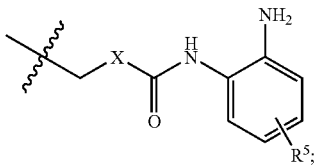

X is a benzene ring or a pyridine ring;
$R^5$ is one or more substituents selected from hydrogen, halo, alkyl, alkoxy or trifluoromethyl.

In the preferred embodiment, the compounds of this invention are those of the formula (I), wherein
  Z is CH;
  $R^1$, $R^2$ and $R^3$ are independently hydrogen, halo, alkyl, alkoxy or trifluoromethyl;
  $R^4$ is

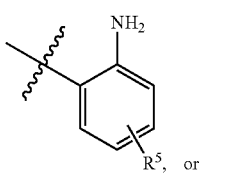

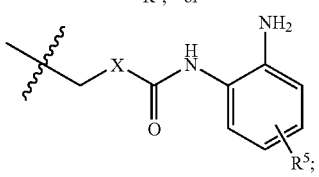

X is a benzene ring or a pyridine ring;
$R^5$ is one or more substituents selected from hydrogen, halo, alkyl, alkoxy or trifluoromethyl.

In another preferred embodiment, the compounds of this invention are those of the formula (I), wherein
  Z is CH;
  $R^1$, $R^2$ and $R^3$ are independently hydrogen or alkoxy;
  $R^4$ is

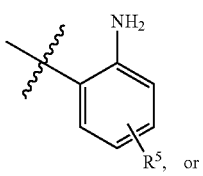

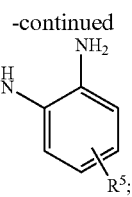

X is a benzene ring or a pyridine ring;
$R^5$ is one or more substituents selected from hydrogen, halo, alkyl, alkoxy or trifluoromethyl.

In another preferred embodiment, the compounds of this invention are those of the formula (I), wherein
  Z is CH;
  $R^1$ and $R^2$ are independently hydrogen or methoxy;
  $R^3$ is H;
  $R^4$ is

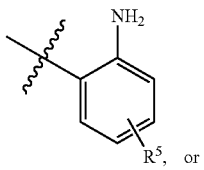

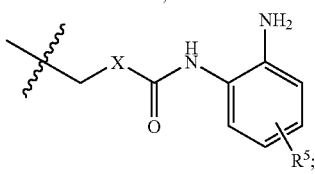

X is a benzene ring or a pyridine ring;
$R^5$ is one or more substituents selected from hydrogen, halo, alkyl, alkoxy or trifluoromethyl.

In another preferred embodiment, the compounds of this invention are those of the formula (I), wherein
  Z is CH;
  $R^1$ and $R^2$ are independently hydrogen or methoxy;
  $R^3$ is H;
  $R^4$ is

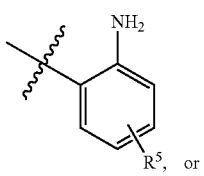

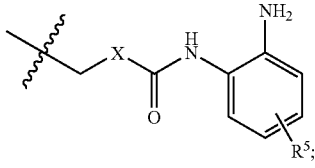

X is a benzene ring or a pyridine ring;
$R^5$ is H or F.

In the above structural formula (I) and throughout the present specification, the following terms have the indicated meaning:

The term "halo" as used herein means fluorine, chlorine, bromine or iodine.

The term "alkyl" as used herein includes methyl, ethyl, n-propyl, iso-propyl, butyl, iso-butyl, sec-butyl, tert-butyl and the like.

The term "alkoxy" as used herein includes methoxy, ethoxy, n-propoxy, isopropoxy, n-butoxy, isobutoxy and the like.

The compounds of this invention can be prepared as follows:

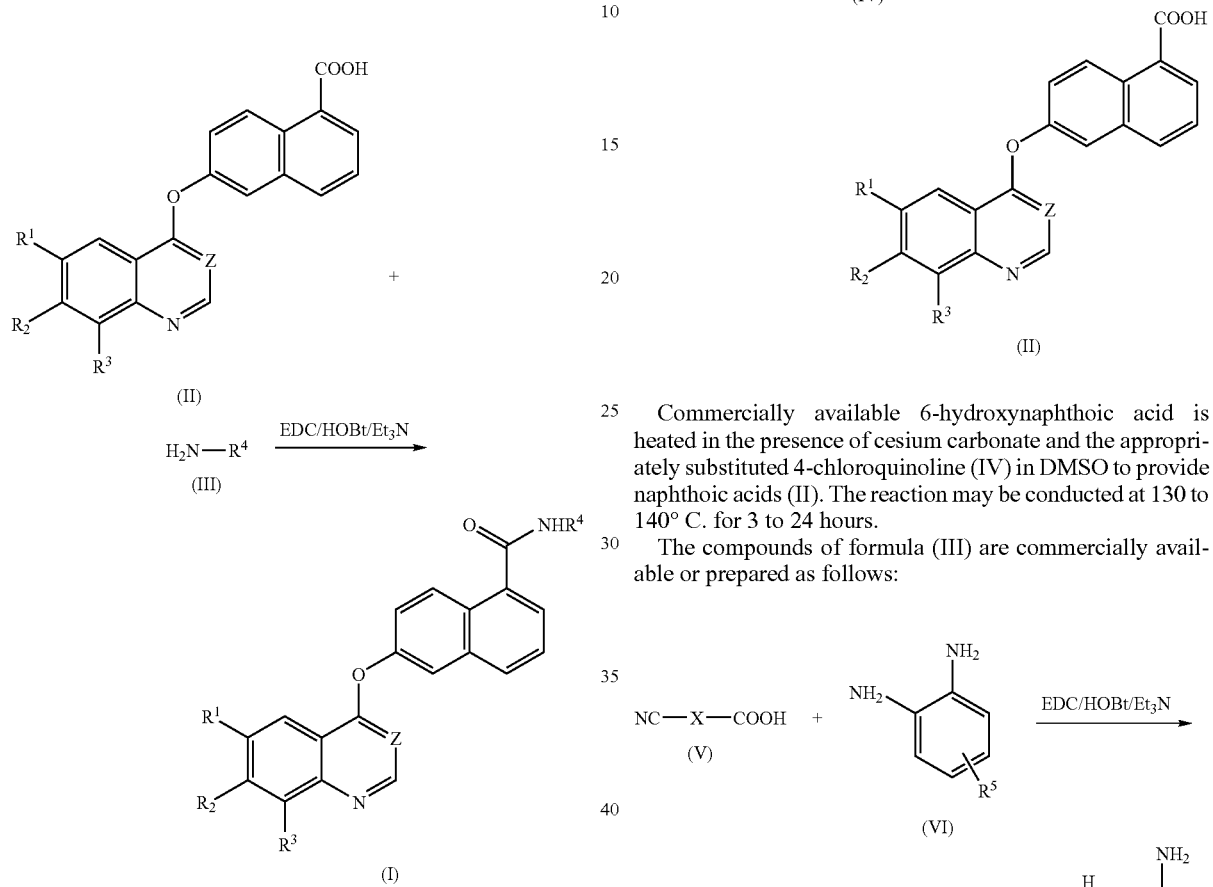

The compound of formula (II) is condensed with a compound of formula (III) to give the title compound (I). The reaction is conducted by using a peptide condensing agent such as 1-Ethyl-3-(3-dimethylaminopropyl)carbodiimide (EDC), dicyclohexylcarbodiimide (DCC), N,N'-carbonyldiimidazole (CDI), etc. The reaction may be conducted at 0 to 80° C. for 4 to 72 hours. Solvents which may be used are normal solvents such as benzene, toluene, tetrahydrofuran, dioxane, dichloromethane, chloroform, N,N-dimethylformamide, etc. If necessary, a base such as sodium hydroxide, triethylamine and pyridine may be added to the reaction system.

The compounds of formula (II) can be prepared as follows:

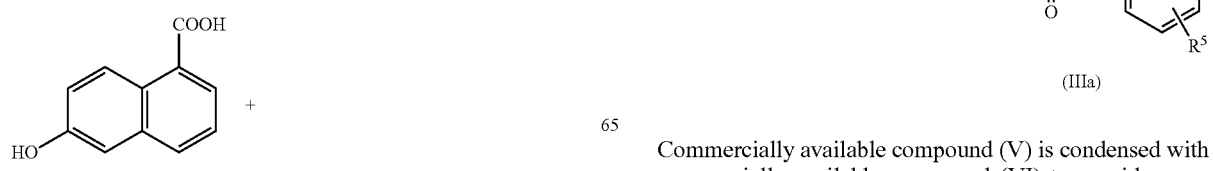

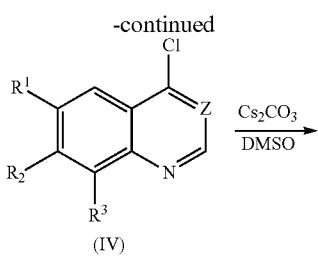

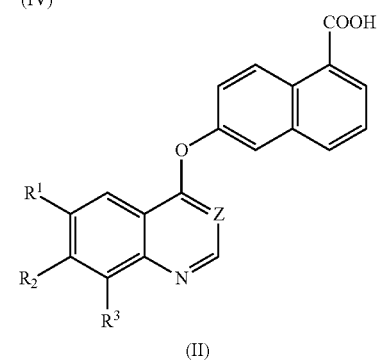

Commercially available 6-hydroxynaphthoic acid is heated in the presence of cesium carbonate and the appropriately substituted 4-chloroquinoline (IV) in DMSO to provide naphthoic acids (II). The reaction may be conducted at 130 to 140° C. for 3 to 24 hours.

The compounds of formula (III) are commercially available or prepared as follows:

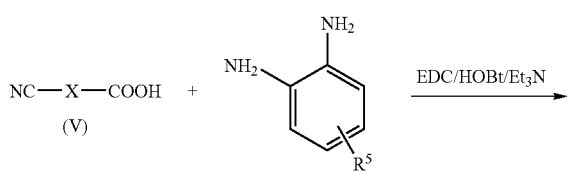

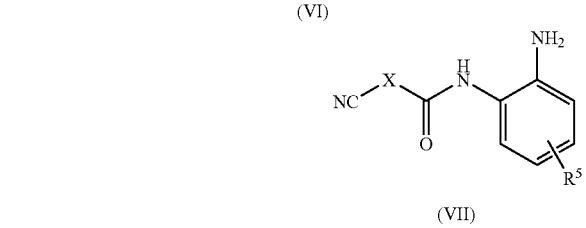

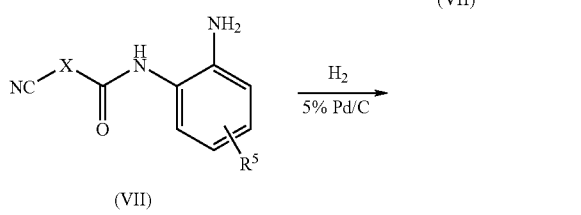

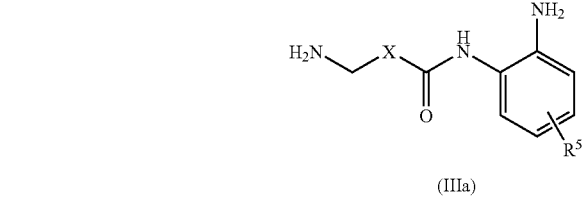

Commercially available compound (V) is condensed with a commercially available compound (VI) to provide compound (VII). The reaction is conducted by using a peptide condensing agent such as 1-Ethyl-3-(3-dimethylaminopropyl)carbodiimide (EDC), dicyclohexylcarbodiimide (DCC), N,N'-carbonyldiimidazole (CDI), etc. The reaction may be conducted at 0 to 60° C. for 2 to 72 hours. Solvents which may be used are normal solvents such as benzene, toluene, tetrahydrofuran, dioxane, dichloromethane, chloroform, N,N-dimethylformamide, etc. If necessary, a base such as sodium hydroxide, triethylamine and pyridine may be added to the reaction system.

The compound (VII) is hydrogenated using 5% palladium on charcoal catalyst in methanol to yield compound (IIIa). The reaction may be conducted at room temperature. If necessary, an acid such as sulfuric acid may be added to the reaction system.

The compounds represented by formula (I) may be purified or isolated by the conventional separation methods such as extraction, recrystallization, column chromatography and the like.

The compounds represented by formula (I) are capable of inhibiting protein kinases and histone deacetylases and are therefore useful in treating diseases associated with abnormal protein kinase activities and abnormal histone deacetylase activities. In particular, they are highly effective against hematological malignancy and solid carcinomas.

The compounds represented by formula (I) useful as a drug may be used in the form of a general pharmaceutical composition. The pharmaceutical composition may be in the forms normally employed, such as tablets, capsules, powders, syrups, solutions, suspensions, aerosols, and the like, may contain flavorants, sweeteners etc. in suitable solids or liquid carriers or diluents, or in suitable sterile media to form injectable solutions or suspensions. Such composition typically contains from 0.5 to 70%, preferably 1 to 20% by weight of active compound, the remainder of the composition being pharmaceutically acceptable carriers, diluents or solvents or salt solutions.

The compounds represented by formula (I) are clinically administered to mammals, including man and animals, via oral, nasal, transdermal, pulmonary, or parenteral routes. Administration by the oral route is preferred, being more convenient and avoiding the possible pain and irritation of injection. By either route, the dosage is in the range of about 0.0001 to 200 mg/kg body weight per day administered singly or as a divided dose. However, the optimal dosage for the individual subject being treated will be determined by the person responsible for treatment, generally smaller dose being administered initially and thereafter increments made to determine the most suitable dosage.

Representative compounds of the present invention are shown in Table 1 below. The compound numbers correspond to the "Example numbers" in the Examples section. That is, the synthesis of compound 16 as shown in the Table 1 is described in "Example 16" and the synthesis of compound 44 as shown in the Table 1 is described in "Example 44". The compounds presented in the Table 1 are exemplary only and are not to be construed as limiting the scope of this invention in any manner.

TABLE 1

| Example | Structure | Name |
| --- | --- | --- |
| 16 | 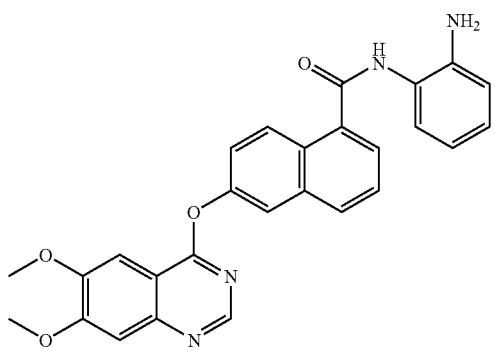 | N-(2-aminophenyl)-6-(6,7-dimethoxyquinazolin-4-yloxy)-1-naphthamide |
| 17 | 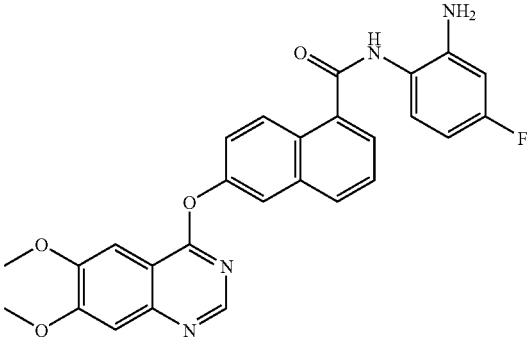 | N-(2-amino-4-fluorophenyl)-6-(6,7-dimethoxyquinazolin-4-yloxy)-1-naphthamide |

TABLE 1-continued
| Example | Structure | Name |
|---|---|---|
| 18 | 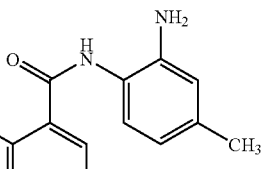 | N-(2-amino-4-methylphenyl)-6-(6,7-dimethoxyquinazolin-4-yloxy)-1-naphthamide |
| 19 | 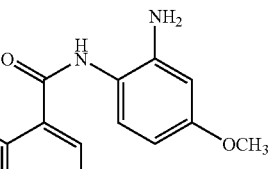 | N-(2-amino-4-methoxyphenyl)-6-(6,7-dimethoxyquinazolin-4-yloxy)-1-naphthamide |
| 20 | 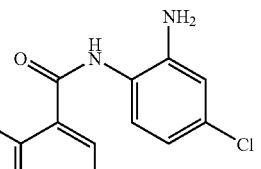 | N-(2-amino-4-chlorophenyl)-6-(6,7-dimethoxyquinazolin-4-yloxy)-1-naphthamide |
| 21 | 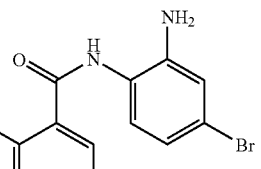 | N-(2-amino-4-bromophenyl)-6-(6,7-dimethoxyquinazolin-4-yloxy)-1-naphthamide |

TABLE 1-continued
| Example | Structure | Name |
|---|---|---|
| 22 | 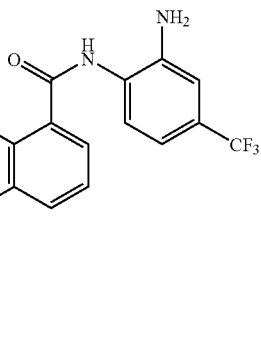 | N-(2-amino-4-trifluoromethyl-phenyl)-6-(6,7-dimethoxy-quinazolin-4-yloxy)-1-naphthamide |
| 23 | 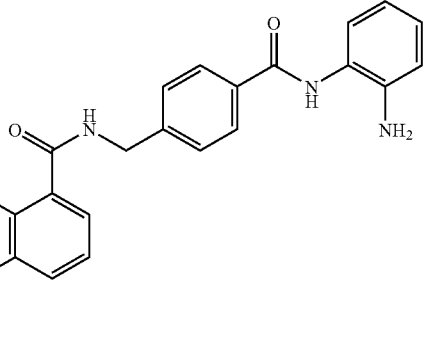 | N-(4-((2-aminophenyl)carbamoyl)-benzyl)-6-(6,7-dimethoxy-quinazolin-4-yloxy)-1-naphthamide |
| 24 | 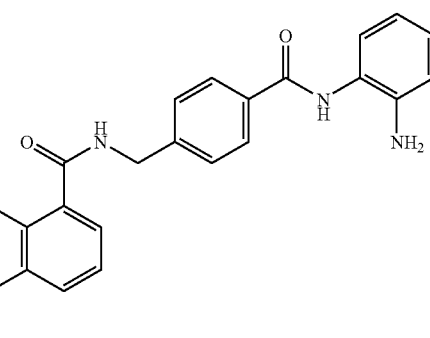 | N-(4-((2-amino-4-fluorophenyl)-carbamoyl)benzyl)-6-(6,7-dimethoxyquinazolin-4-yloxy)-1-naphthamide |

TABLE 1-continued

| Example | Structure | Name |
|---|---|---|
| 25 | 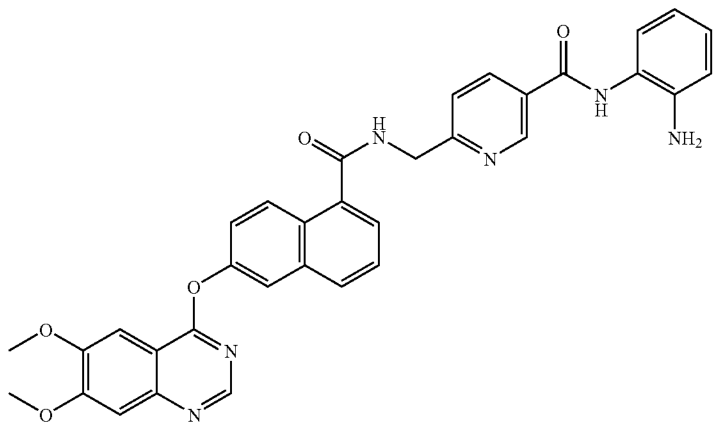 | N-(2-aminophenyl)-6-((2-(6,7-dimethoxyquinazolin-4-yloxy)-1-naphthamido)methyl)nicotinamide |
| 26 | 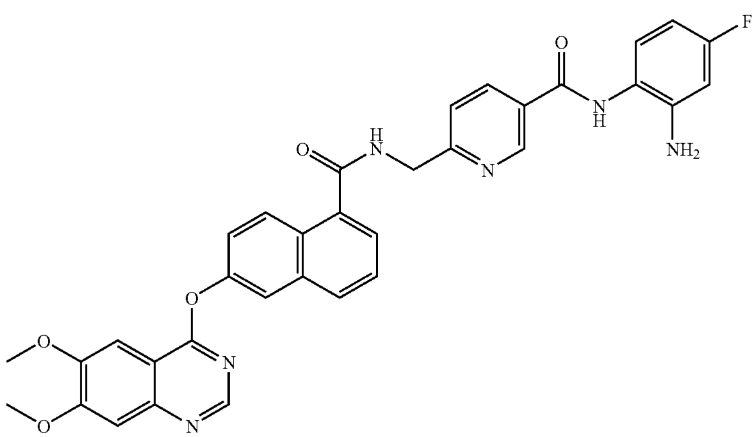 | N-(2-amino-4-fluorophenyl)-6-((2-(6,7-dimethoxyquinazolin-4-yloxy)-1-naphthamido)methyl)-nicotinamide |
| 27 | 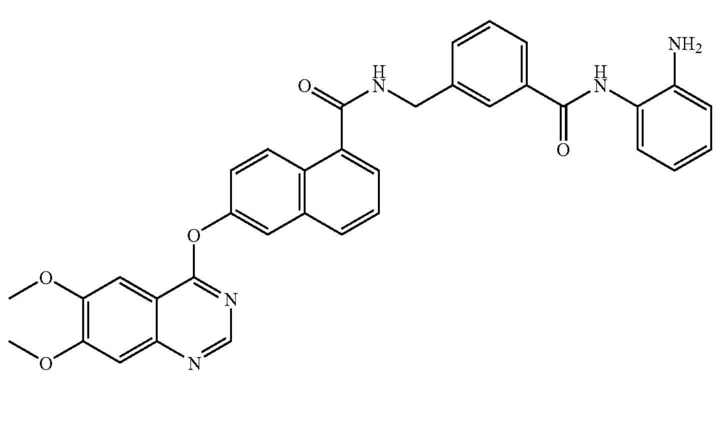 | N-(3((2-aminophenyl)carbamoyl)-benzyl)-6-(6,7-dimethoxy-quinazolin-4-yloxy)-1-naphthamide |

TABLE 1-continued

| Example | Structure | Name |
|---|---|---|
| 28 | 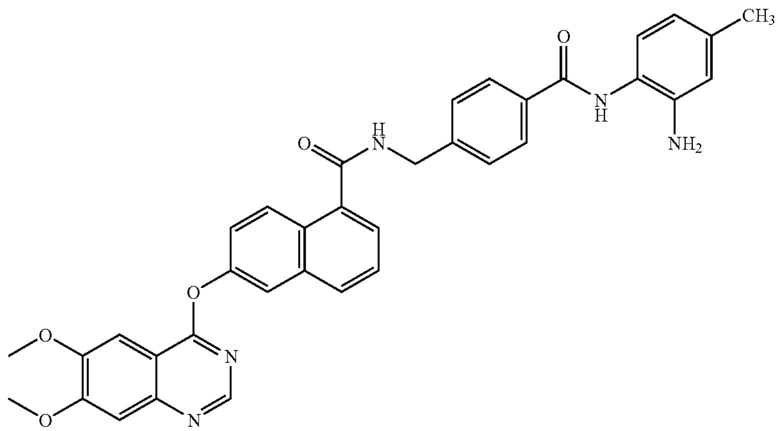 | N-(4-((2-amino-4-methylphenyl)-carbamoyl)benzyl)-6-(6,7-dimethoxyquinazolin-4-yloxy)-1-naphthamide |
| 29 | 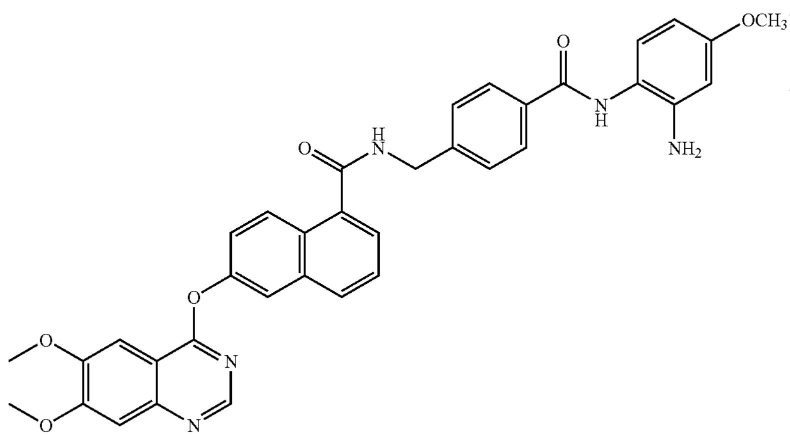 | N-(4-((2-amino-4-methoxyphenyl)-carbamoyl)benzyl)-6-(6,7-dimethoxyquinazolin-4-yloxy)-1-naphthamide |
| 30 | 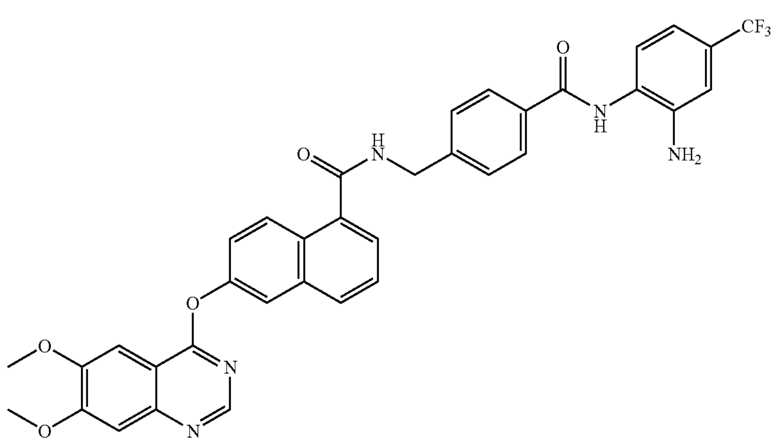 | N-(4-((2-amino-4-trifluoromethyl-phenyl)carbamoyl)benzyl)-6-(6,7-dimethoxyquinazolin-4-yloxy)-1-naphthamide |

TABLE 1-continued

| Example | Structure | Name |
|---|---|---|
| 31 | 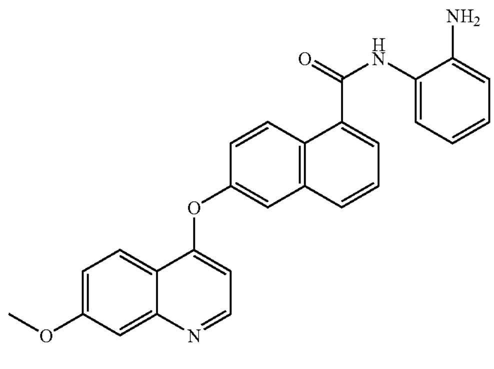 | N-(2-aminophenyl)-6-(7-methoxyquinolin-4-yloxy)-1-naphthamide |
| 32 | 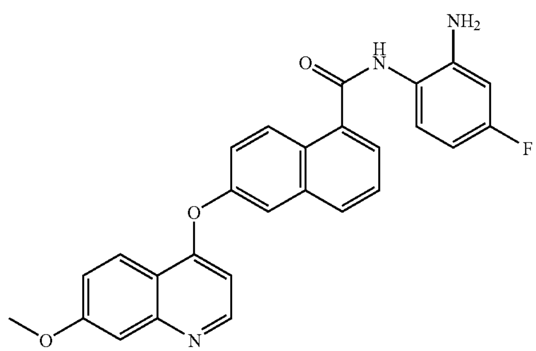 | N-(2-amino-4-fluorophenyl)-6-(7-methoxyquinolin-4-yloxy)-1-naphthamide |
| 33 | 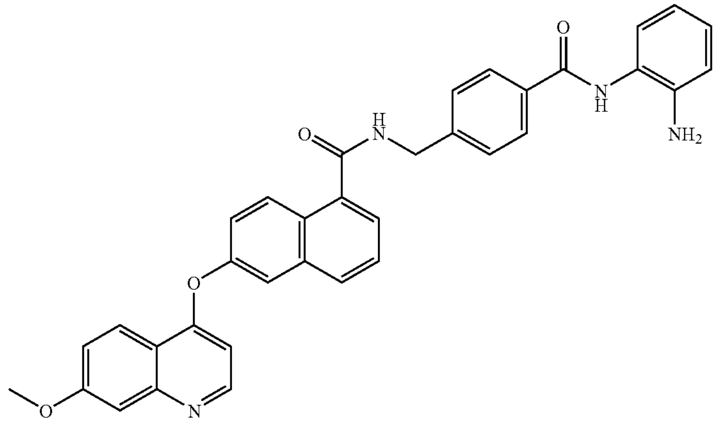 | N-(4-((2-aminophenyl)carbamoyl)-benzyl)-6-(7-methoxyquinolin-4-yloxy)-1-naphthamide |
| 34 | 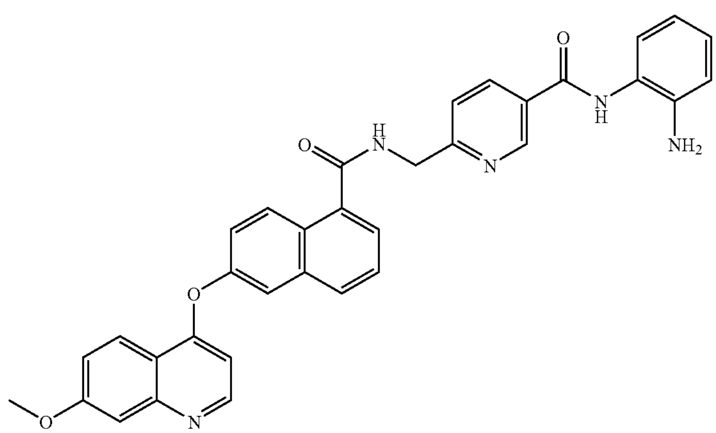 | N-(2-aminophenyl)-6-((2-(7-methoxyquinolin-4-yloxy)-1-naphthamido)methyl)nicotinamide |

TABLE 1-continued

| Example | Structure | Name |
|---|---|---|
| 35 | 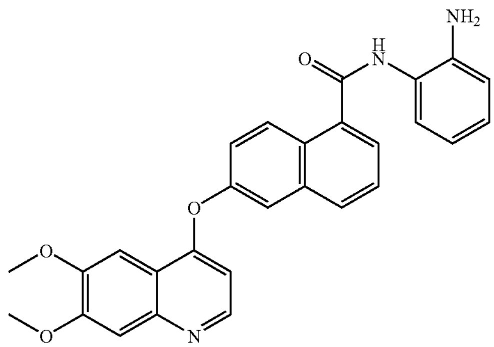 | N-(2-aminophenyly 6-(6,7-dimethoxyquinolin-4-yloxy)-1-naphthamide |
| 36 | 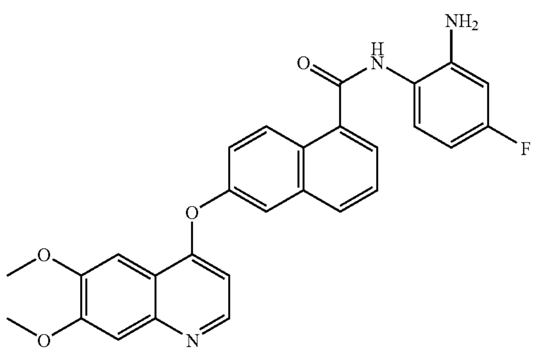 | N-(2-amino-4-fluorophenyl)-6-(6,7-dimethoxyquinolin-4-yloxy)-1-naphthamide |
| 37 | 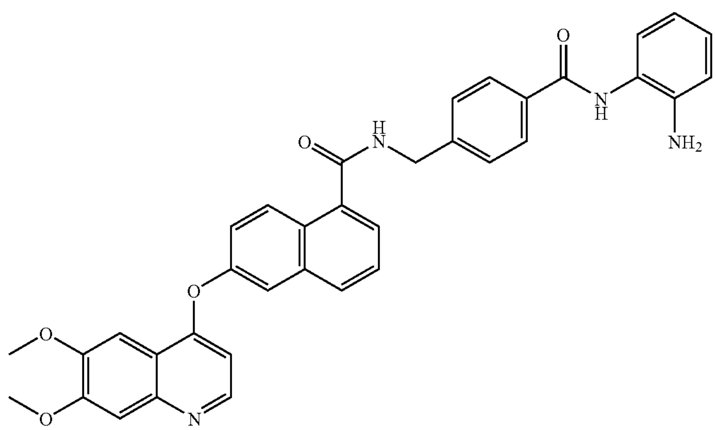 | N-(4-((2-aminophenyl)carbamoyl)-benzyl)-6-(6,7-dimethoxy-quinolin-4-yloxy)-1-naphthamide |
| 38 | 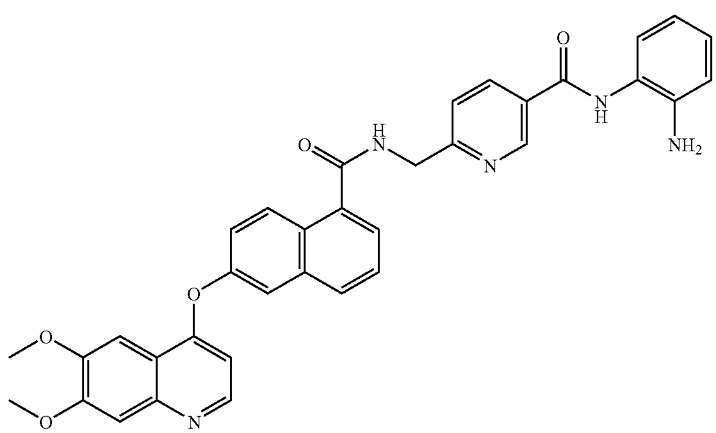 | N-(2-aminophenyl)-6-((2-(6,7-dimethoxyquinolin-4-yloxy)-1-naphthamido)methyl)nicotinamide |

TABLE 1-continued

| Example | Structure | Name |
| --- | --- | --- |
| 39 | 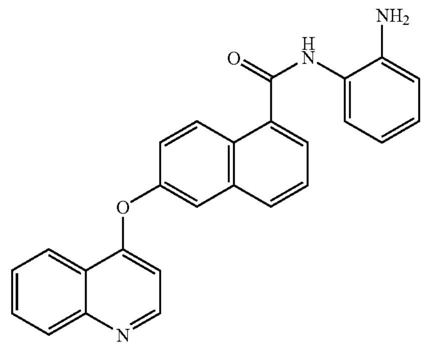 | N-(2-aminophenyl)-6-(quinolin-4-yloxy)-1-naphthamide |
| 40 | 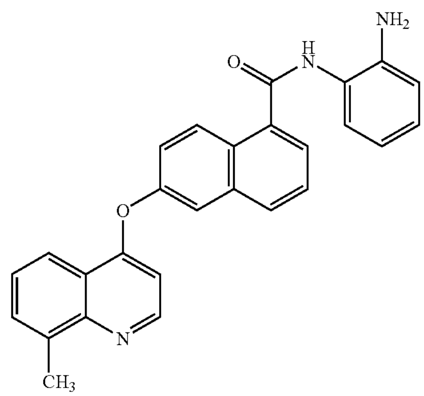 | N-(2-aminophenyl)-6-(8-methyl-quinolin-4-yloxy)-1-naphthamide |
| 41 | 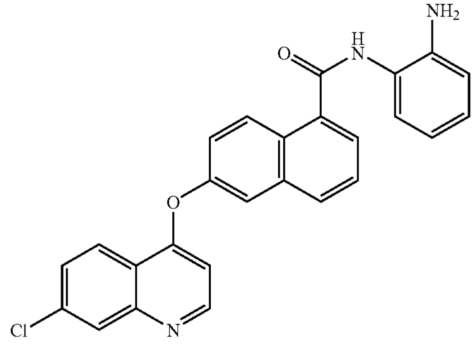 | N-(2-aminophenyl)-6-(7-chloro-quinolin-4-yloxy)-1-naphthamide |

TABLE 1-continued

| Example | Structure | Name |
|---|---|---|
| 42 | 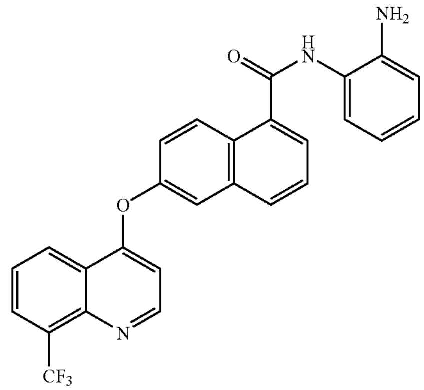 | N-(2-aminophenyl)-6-(8-(trifluoromethyl)quinolin-4-yloxy)-1-naphthamide |
| 43 | 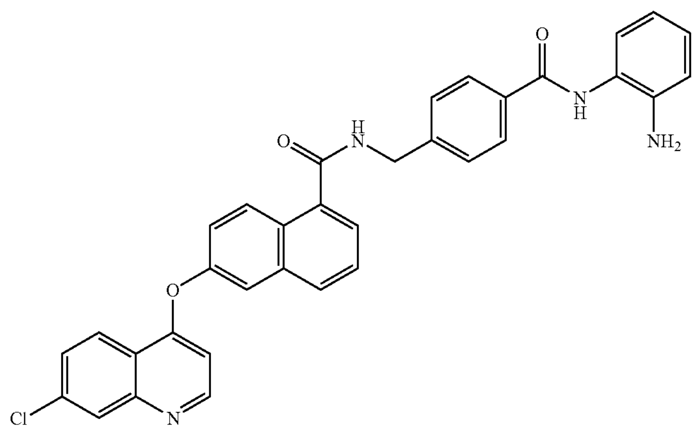 | N-(4-((2-aminophenyl)carbamoyl)-benzyl)-6-(7-chloroquinolin-4-yloxy)-1-naphthamide |
| 44 | 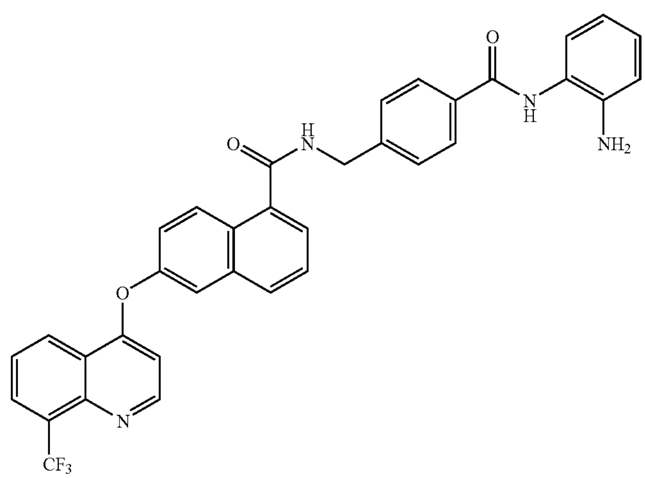 | N-(4-((2-((2-aminophenyl)carbamoyl)-benzyl)-6-(8-(trifluoromethyl)-quinolin-4-yloxy)-1-naphthamide |

Further, all parts and percentages in the examples, as well as in the remainder of the specification, are by weight unless otherwise specified. Any range of numbers recited in the specification or paragraphs hereinafter describing or claiming various aspects of the invention, such as that representing a particular set of properties, units of measure, conditions, physical states or percentages, is intended to literally incorporate expressly herein by reference or otherwise, any number falling within such range, including any subset of numbers or ranges subsumed within any range so recited. The term "about" when used as a modifier for, or in conjunction with, a variable, is intended to convey that the numbers and ranges disclosed herein are flexible and that practice of the present invention by those skilled in the art using temperatures, concentrations, amounts, contents, carbon numbers, and properties that are outside of the range or different from a single value, will achieve the desired result.

EXAMPLE 1

Preparation of 6-(6,7-dimethoxyquinazolin-4-yloxy)-1-naphthoic acid

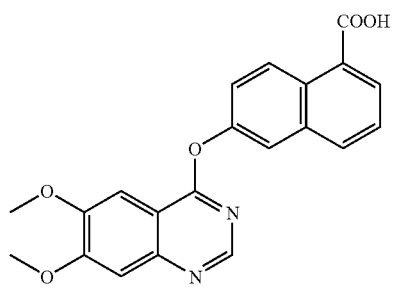

6-Hydroxy-1-naphthoic acid (1.43 g, 7.6 mmol) and 38 ml of DMSO were stirred at room temperature while cesium carbonate (7.5 g, 22.9 mmol) and 4-chloro-6,7-dimethoxyquinazoline (2.05 g, 9.14 mmol) were added. The mixture was heated at 140° C. for 3 hours. The mixture was cooled to room temperature and diluted with 40 mL of H$_2$O. The mixture was neutralized with 2 N HCl to 6.5. The deposited solids were collected by vacuum filtration, washed with H$_2$O, dried under vacuum and recrystallized from methanol to give the title compound (1.68 g, 59% yield) as a brown solid. LC-MS (m/z) 377 (M+1).

EXAMPLE 2

Preparation of 6-(7-methoxyquinolin-4-yloxy)-1-naphthoic acid

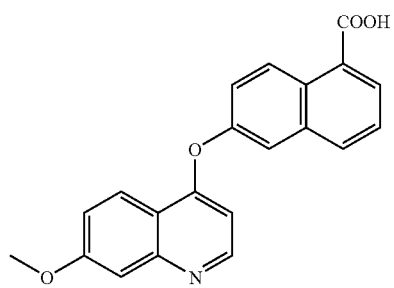

The title compound (1.73 g, 66% yield) was prepared as a brown solid from 6-hydroxy-1-naphthoic acid (1.43 g, 7.6 mmol) and 4-chloro-7-methoxyquinoline (1.77 g, 9.14 mmol) by an analogous procedure to that described in example 1. LC-MS (m/z) 346 (M+1).

EXAMPLE 3

Preparation of 6-(6,7-dimethoxyquinolin-4-yloxy)-1-naphthoic acid

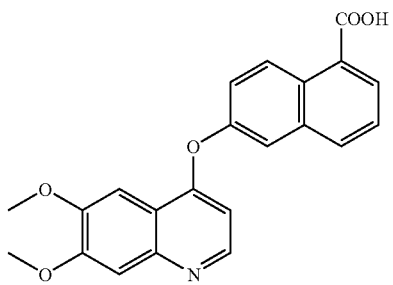

The title compound (1.95 g, 68% yield) was prepared as a brown solid from 6-hydroxy-1-naphthoic acid (1.43 g, 7.6 mmol) and 4-chloro-6,7-dimethoxyquinoline (2.04 g, 9.14 mmol) by an analogous procedure to that described in example 1. LC-MS (m/z) 376 (M+1).

EXAMPLE 4

Preparation of 6-(quinolin-4-yloxy)-1-naphthoic acid

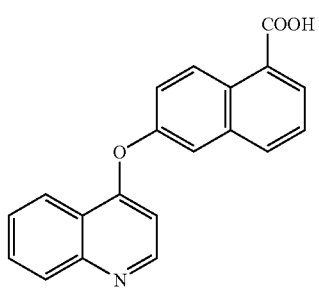

The title compound (1.24 g, 52% yield) was prepared as a brown solid from 6-hydroxy-1-naphthoic acid (1.43 g, 7.6 mmol) and 4-chloroquinoline (1.49 g, 9.14 mmol) by an analogous procedure to that described in example 1. LC-MS (m/z) 316 (M+1).

EXAMPLE 5

Preparation of 6-(8-methylquinolin-4-yloxy)-1-naphthoic acid

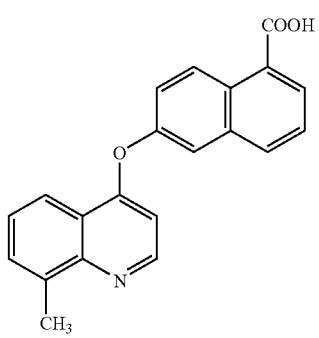

The title compound (1.25 g, 55% yield) was prepared as a brown solid from 6-hydroxy-1-naphthoic acid (1.43 g, 7.6 mmol) and 4-chloro-8-methylquinoline (1.62 g, 9.14 mmol) by an analogous procedure to that described in example 1. LC-MS (m/z) 330 (M+1).

EXAMPLE 6

Preparation of 6-(7-chloroquinolin-4-yloxy)-1-naphthoic acid

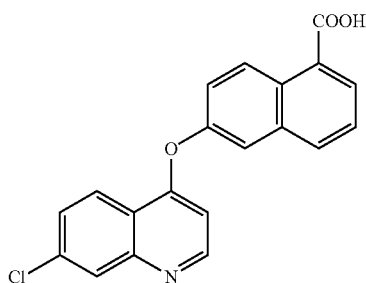

The title compound (1.57 g, 59% yield) was prepared as a brown solid from 6-hydroxy-1-naphthoic acid (1.43 g, 7.6 mmol) and 4,7-dichloroquinoline (1.81 g, 9.14 mmol) by an analogous procedure to that described in example 1. LC-MS (m/z) 350 (M+1).

EXAMPLE 7

Preparation of 6-(8-(trifluoromethyl)quinolin-4-yloxy)-1-naphthoic acid

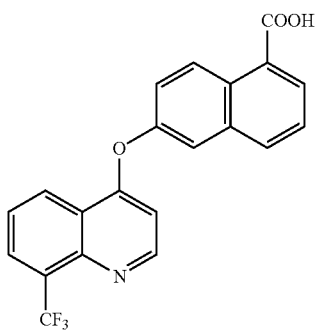

The title compound (1.43 g, 49% yield) was prepared as a brown solid from 6-hydroxy-1-naphthoic acid (1.43 g, 7.6 mmol) and 4-chloro-8-(trifluoromethyl)quinoline (2.12 g, 9.14 mmol) by an analogous procedure to that described in example 1. LC-MS (m/z) 384 (M+1).

EXAMPLE 8

Preparation of 4-(aminomethyl)-N-(2-aminophenyl)benzamide

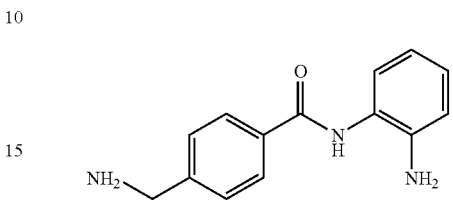

4-Cyanobenzoic acid (294 mg, 2 mmol) and 8 ml of DMF were stirred at room temperature while 1-Ethyl-3-(3-dimethylaminopropyl)carbodiimide hydrochloride (768 mg, 4 mmol), hydroxybenzotriazole (324 mg, 2.4 mmol), triethylamine (808 mg, 8 mmol) and o-phenylenediamine (432 mg, 4 mmol) were added. The mixture was stirred for 20 hours at room temperature. The mixture was diluted with 400 mL of brine. The solids were collected by vacuum filtration, washed with water and dried under vacuum to give N-(2-aminophenyl)-4-cyanobenzamide (364 mg, 77%) as a grey solid. LC-MS (m/z) 238 (M+1).

To a solution of N-(2-aminophenyl)-4-cyanobenzamide (237 mg, 1 mmol) in methanol (40 ml) was added sulfuric acid (196 mg, 1 mmol) and 5% palladium on charcoal (0.20 g). The mixture was stirred under an atmosphere of hydrogen at room temperature until hydrogen uptake ceased. The mixture was filtered through celite, and the filtrate was neutralized with 1 N NaOH solution in methanol (2 ml). The resulting mixture was filtered, and the filtrate was evaporated under vacuum to give the title compound (232 mg, 96% yield) as a grey solid. LC-MS (m/z) 242 (M+1).

EXAMPLE 9

Preparation of 4-(aminomethyl)-N-(2-amino-4-fluorophenyl)benzamide

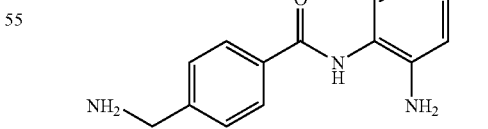

The title compound (186 mg, 72% yield) was prepared as a brown solid from 4-cyano-benzoic acid (294 mg, 2 mmol) and 4-fluoro-o-phenylenediamine (302 mg, 2.4 mmol) by an analogous procedure to that described in example 8. LC-MS (m/z) 260 (M+1).

EXAMPLE 10

Preparation of 4-(aminomethyl)-N-(2-amino-4-methylphenyl)benzamide

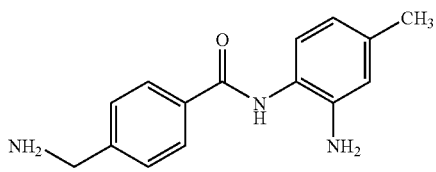

The title compound (173 mg, 68% yield) was prepared as a grey solid from 4-cyano-benzoic acid (294 mg, 2 mmol) and 4-methyl-o-phenylenediamine (293 mg, 2.4 mmol) by an analogous procedure to that described in example 8. LC-MS (m/z) 256 (M+1).

EXAMPLE 11

Preparation of 4-(aminomethyl)-N-(2-amino-4-methoxyphenyl)benzamide

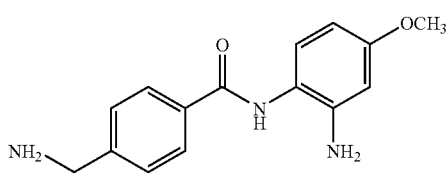

The title compound (192 mg, 71% yield) was prepared as a grey solid from 4-cyano-benzoic acid (294 mg, 2 mmol) and 4-methoxy-o-phenylenediamine (331 mg, 2.4 mmol) by an analogous procedure to that described in example 8. LC-MS (m/z) 272 (M+1).

EXAMPLE 12

Preparation of 4-(aminomethyl)-N-(2-amino-4-trifluoromethylphenyl)benzamide

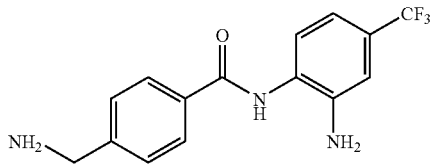

The title compound (195 mg, 63% yield) was prepared as a grey solid from 4-cyano-benzoic acid (294 mg, 2 mmol) and 4-trifluoromethyl-o-phenylenediamine (422 mg, 2.4 mmol) by an analogous procedure to that described in example 8. LC-MS (m/z) 310 (M+1).

EXAMPLE 13

Preparation of 3-(aminomethyl)-N-(2-aminophenyl)benzamide

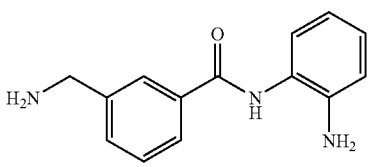

The title compound (140 mg, 58% yield) was prepared as a grey solid from 3-cyano-benzoic acid (294 mg, 2 mmol) and o-phenylenediamine (432 mg, 4 mmol) by an analogous procedure to that described in example 8. LC-MS (m/z) 242 (M+1).

EXAMPLE 14

Preparation of 6-(aminomethyl)-N-(2-aminophenyl)nicotinamide

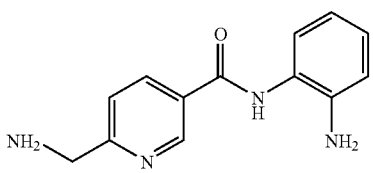

The title compound (157 mg, 65% yield) was prepared as a grey solid from 6-cyano-nicotinic acid (296 mg, 2 mmol) and o-phenylenediamine (864 mg, 8 mmol) by an analogous procedure to that described in example 8. LC-MS (m/z) 243 (M+1).

EXAMPLE 15

Preparation of 6-(aminomethyl)-N-(2-amino-4-fluorophenyl)nicotinamide

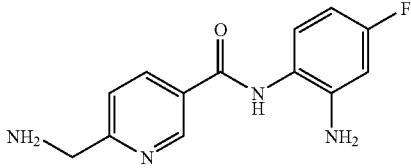

The title compound (135 mg, 52% yield) was prepared as a grey solid from 6-cyano-nicotinic acid (296 mg, 2 mmol) and 4-fluoro-o-phenylenediamine (302 mg, 2.4 mmol) by an analogous procedure to that described in example 8. LC-MS (m/z) 261 (M+1).

EXAMPLE 16

Preparation of N-(2-aminophenyl)-6-(6,7-dimethoxyquinazolin-4-yloxy)-1-naphthamide

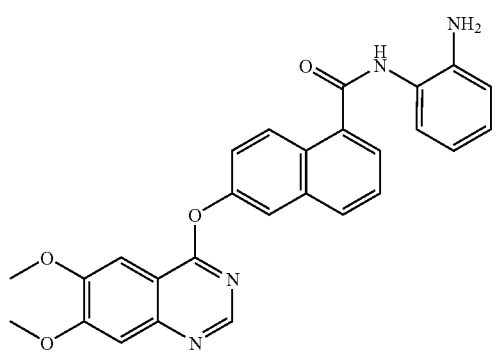

6-(6,7-Dimethoxyquinazolin-4-yloxy)-1-naphthoic acid (37.6 mg, 0.1 mmol) and 4 ml of DMF were stirred at room temperature while 1-Ethyl-3-(3-dimethyllaminopropyl)carbodiimide hydrochloride (38.4 mg, 0.2 mmol), hydroxybenzotriazole (16.2 mg, 0.12 mmol), triethylamine (40.4 mg, 0.4 mmol) and o-phenylenediamine (43.2 mg, 0.4 mmol) were added. The mixture was stirred for 20 hours at room temperature. The mixture was diluted with 200 mL of brine. The solids were collected by vacuum filtration, washed with water and dried under vacuum to give the title compound (39.1 mg, 84%) as a brown solid. $^1$H NMR (DMSO-$d_6$) δ 4.01 (s, 6H, 2×OCH$_3$), 4.97 (s, 2H, benzene-NH$_2$), 6.65 (t, J=7.2 Hz, 1H, Ar—H), 6.82 (d, J=7.0 Hz, 1H, Ar—H), 7.00 (t, J=7.1 Hz, 1H, Ar—H), 7.38 (d, J=7.1 Hz, 1H, Ar—H), 7.42 (s, 1H, Ar—H), 7.60 (dd, J=2.4 and 9.2 Hz, 1H, Ar—H), 7.64-7.68 (m, 2H, Ar—H), 7.87 (d, J=6.7 Hz, 1H, Ar—H), 7.97 (d, J=2.3 Hz, 1H, Ar—H), 8.09 (d, J=8.2 Hz, 1H, Ar—H), 8.38 (d, J=9.2 Hz, 1H, Ar—H), 8.54 (s, 1H, Ar—H), 9.85 (s, 1H, benzene-NH). LC-MS (m/z) 467 (M+1).

EXAMPLE 17

Preparation of N-(2-amino-4-fluorophenyl)-6-(6,7-dimethoxyquinazolin-4-yloxy)-1-naphthamide

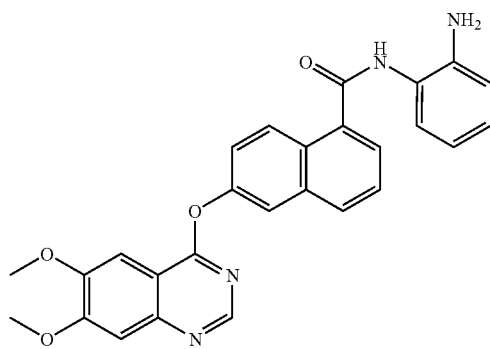

The title compound (43.1 mg, 89% yield) was prepared as a brown solid from 6-(6,7-dimethoxyquinazolin-4-yloxy)-1-naphthoic acid (37.6 mg, 0.1 mmol) and 4-fluoro-o-phenylenediamine (15.1 mg, 0.12 mmol) by an analogous procedure to that described in example 16. $^1$H NMR (DMSO-$d_6$) δ 4.01 (s, 6H, 2×OCH$_3$), 5.28 (s, 2H, benzene-NH$_2$), 6.41 (td, J=2.6 and 8.5 Hz, 1H, Ar—H), 6.59 (dd, J=2.6 and 11.2 Hz, 1H, Ar—H), 7.35 (td, J=1.8 and 7.5 Hz, 1H, Ar—H), 7.41 (s, 1H, Ar—H), 7.59 (dd, J=2.2 and 8.4 Hz, 1H, Ar—H), 7.63-7.67 (m, 2H, Ar—H), 7.89 (d, J=6.9 Hz, 1H, Ar—H), 7.96 (d, J=1.9 Hz, 1H, Ar—H), 8.08 (d, J=8.2 Hz, 1H, Ar—H), 8.38 (d, J=9.2 Hz, 1H, Ar—H), 8.54 (s, 1H, Ar—H), 9.77 (s, 1H, benzene-NH). LC-MS (m/z) 485 (M+1).

EXAMPLE 18

Preparation of N-(2-amino-4-methylphenyl)-6-(6,7-dimethoxyquinazolin-4-yloxy)-1-naphthamide

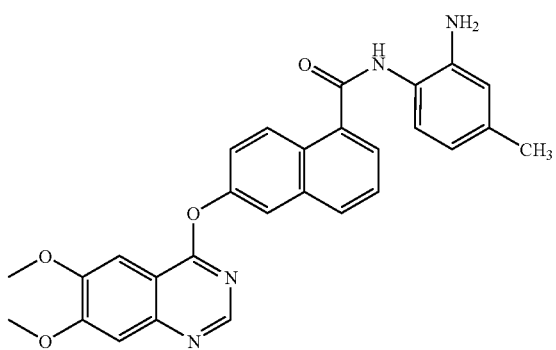

The title compound (39.4 mg, 82% yield) was prepared as a brown solid from 6-(6,7-dimethoxyquinazolin-4-yloxy)-1-naphthoic acid (37.6 mg, 0.1 mmol) and 4-methyl-o-phenylenediamine (14.6 mg, 0.12 mmol) by an analogous procedure to that described in example 16. $^1$H NMR (DMSO-$d_6$) (isomer ratio 0.77/0.23) δ 2.21 (s, 1H, Ar—CH$_3$), 4.01 (s, 6H, 2×OCH$_3$), 4.77 (s, 0.23×2H, benzene-NH$_2$), 4.89 (s, 0.77× 2H, benzene-NH$_2$), 6.46 (d, J=7.6 Hz, 0.77×1H, Ar—H), 6.64 (s, 0.77×1H, Ar—H), 6.73 (d, J=7.9 Hz, 0.23×1H, Ar—H), 6.81 (s, 0.23×1H, Ar—H), 7.24 (d, J=8.1 Hz, 1H, Ar—H), 7.41 (s, 1H, Ar—H), 7.58-7.66 (m, 3H, Ar—H), 7.85 (d, J=6.7 Hz, 1H, Ar—H), 7.97 (s, 1H, Ar—H), 8.08 (d, J=7.9 Hz, 1H, Ar—H), 8.38 (d, J=9.0 Hz, 1H, Ar—H), 8.54 (s, 1H, Ar—H), 9.77 (s, 1H, benzene-NH). LC-MS (m/z) 481 (M+1).

EXAMPLE 19

Preparation of N-(2-amino-4-methoxyphenyl)-6-(6,7-dimethoxyquinazolin-4-yloxy)-1-naphthamide

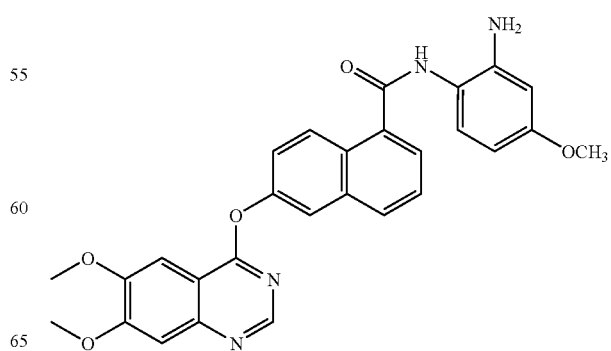

The title compound (43.2 mg, 87% yield) was prepared as a brown solid from 6-(6,7-dimethoxyquinazolin-4-yloxy)-1-naphthoic acid (37.6 mg, 0.1 mmol) and 4-methoxy-o-phenylenediamine (16.5 mg, 0.12 mmol) by an analogous procedure to that described in example 16. $^1$H NMR (DMSO-$d_6$) δ 3.70 (s, 3H, —OCH$_3$), 4.01 (s, 6H, 2×OCH$_3$), 5.00 (s, 2H, benzene-NH$_2$), 6.23 (dd, J=2.6 and 8.6 Hz, 1H, Ar—H), 6.40 (d, J=2.6 Hz, 1H, Ar—H), 7.22 (d, J=8.6 Hz, 1H, Ar—H), 7.41 (s, 1H, Ar—H), 7.59 (dd, J=2.2 and 9.1 Hz, 1H, Ar—H), 7.62-7.66 (m, 2H, Ar—H), 7.86 (d, J=6.9 Hz, 1H, Ar—H), 7.96 (d, J=2.0 Hz, 1H, Ar—H), 8.07 (d, J=8.2 Hz, 1H, Ar—H), 8.38 (d, J=9.2 Hz, 1H, Ar—H), 8.54 (s, 1H, Ar—H), 9.70 (s, 1H, benzene-NH). LC-MS (m/z) 497 (M+1).

EXAMPLE 20

Preparation of N-(2-amino-4-chlorophenyl)-6-(6,7-dimethoxyquinazolin-4-yloxy)-1-naphthamide

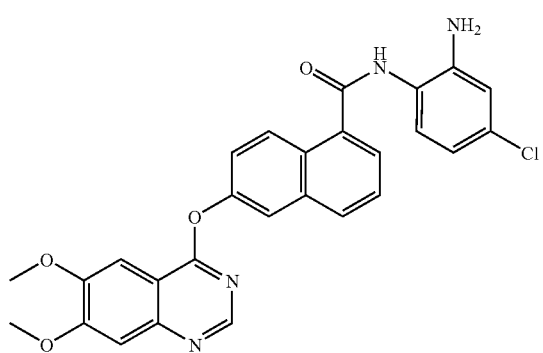

The title compound (42.9 mg, 83% yield) was prepared as a brown solid from 6-(6,7-dimethoxyquinazolin-4-yloxy)-1-naphthoic acid (37.6 mg, 0.1 mmol) and 4-chloro-o-phenylenediamine (17.1 mg, 0.12 mmol) by an analogous procedure to that described in example 16. $^1$H NMR (DMSO-$d_6$) δ 4.01 (s, 6H, 2×OCH$_3$), 5.31 (s, 2H, benzene-NH$_2$), 6.65 (d, J=8.3 Hz, 1H, Ar—H), 6.86 (d, J=1.9 Hz, 1H, Ar—H), 7.41 (s, 1H, Ar—H), 7.58-7.67 (m, 4H, Ar—H), 7.89 (d, J=6.8 Hz, 1H, Ar—H), 8.01 (s, 1H, Ar—H), 8.09 (d, J=8.1 Hz, 1H, Ar—H), 8.37 (d, J=9.2 Hz, 1H, Ar—H), 8.55 (s, 1H, Ar—H), 9.84 (s, 1H, benzene-NH). LC-MS (m/z) 501 (M+1).

EXAMPLE 21

Preparation of N-(2-amino-4-bromophenyl)-6-(6,7-dimethoxyquinazolin-4-yloxy)-1-naphthamide

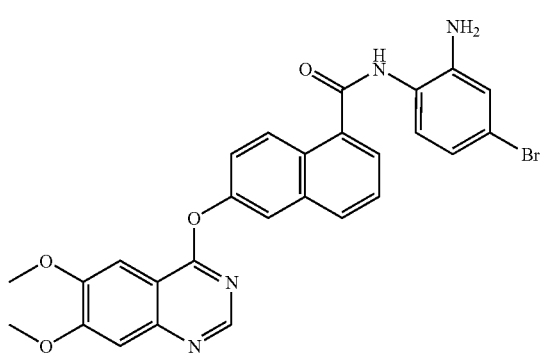

The title compound (42.0 mg, 77% yield) was prepared as a brown solid from 6-(6,7-dimethoxyquinazolin-4-yloxy)-1-naphthoic acid (37.6 mg, 0.1 mmol) and 4-bromo-o-phenylenediamine (22.4 mg, 0.12 mmol) by an analogous procedure to that described in example 16. $^1$H NMR (DMSO-$d_6$) δ 4.01 (s, 6H, 2×OCH$_3$), 5.31 (s, 2H, benzene-NH$_2$), 6.77 (d, J=8.3 Hz, 1H, Ar—H), 7.01 (s, 1H, Ar—H), 7.41 (s, 1H, Ar—H), 7.58-7.65 (m, 5H, Ar—H), 7.89 (d, J=7.0 Hz, 1H, Ar—H), 8.00 (s, 1H, Ar—H), 8.14 (d, J=10.2 Hz, 1H, Ar—H), 8.37 (d, J=9.1 Hz, 1H, Ar—H), 8.54 (s, 1H, Ar—H), 9.84 (s, 1H, benzene-NH). LC-MS (m/z) 545 (M+1).

EXAMPLE 22

Preparation of N-(2-amino-4-trifluoromethylphenyl)-6-(6,7-dimethoxyquinazolin-4-yloxy)-1-naphthamide

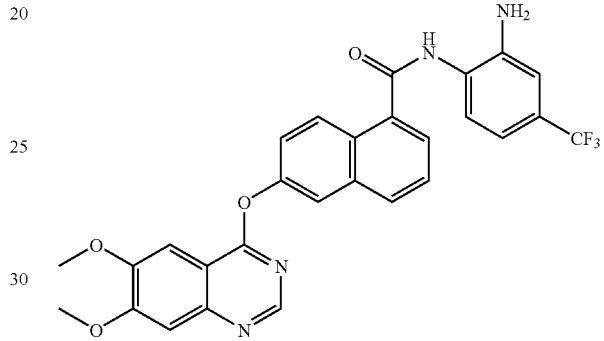

The title compound (42.3 mg, 79% yield) was prepared as a brown solid from 6-(6,7-dimethoxyquinazolin-4-yloxy)-1-naphthoic acid (37.6 mg, 0.1 mmol) and 4-trifluoromethyl-o-phenylenediamine (21.1 mg, 0.12 mmol) by an analogous procedure to that described in example 16. $^1$H NMR (DMSO-$d_6$) δ 4.01 (s, 6H, 2×OCH$_3$), 5.72 (s, 2H, benzene-NH$_2$), 6.92 (d, J=8.5 Hz, 1H, Ar—H), 7.42 (s, 1H, Ar—H), 7.59-7.65 (m, 3H, Ar—H), 7.90-7.96 (m, 2H, Ar—H), 7.98 (s, 1H, Ar—H), 8.10 (d, J=8.3 Hz, 1H, Ar—H), 8.17 (d, J=7.3 Hz, 1H, Ar—H), 8.39 (d, J=9.2 Hz, 1H, Ar—H), 8.54 (s, 1H, Ar—H), 9.90 (s, 1H, benzene-NH). LC-MS (m/z) 535 (M+1).

EXAMPLE 23

Preparation of N-(4-((2-aminophenyl)carbamoyl)benzyl)-6-(6,7-dimethoxyquinazolin-4-yloxy)-1-naphthamide

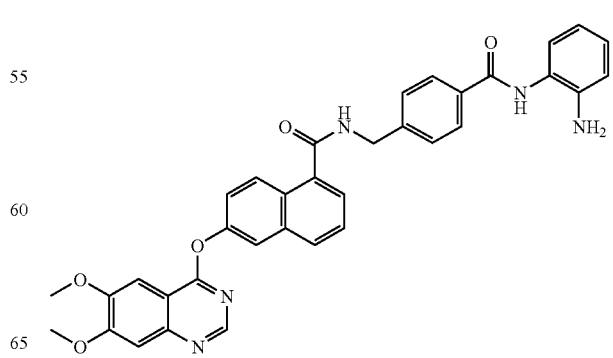

The title compound (43.1 mg, 72% yield) was prepared as a brown solid from 6-(6,7-dimethoxyquinazolin-4-yloxy)-1-naphthoic acid (37.6 mg, 0.1 mmol) and 4-(aminomethyl)-N-(2-aminophenyl)benzamide (28.9 mg, 0.12 mmol) by an analogous procedure to that described in example 16. LC-MS (m/z) 600 (M+1).

EXAMPLE 24

Preparation of N-(4-((2-amino-4-fluorophenyl)carbamoyl)benzyl)-6-(6,7-dimethoxyquinazolin-4-yloxy)-1-naphthamide

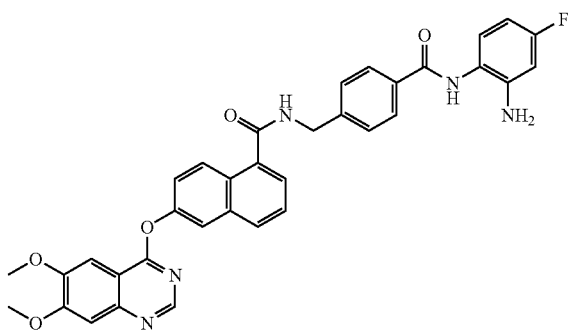

The title compound (46.3 mg, 75% yield) was prepared as a brown solid from 6-(6,7-dimethoxyquinazolin-4-yloxy)-1-naphthoic acid (37.6 mg, 0.1 mmol) and 4-(aminomethyl)-N-(2-amino-4-fluorophenyl)benzamide (31.1 mg, 0.12 mmol) by an analogous procedure to that described in example 16. LC-MS (m/z) 618 (M+1).

EXAMPLE 25

Preparation of N-(2-aminophenyl)-6-((2-(6,7-dimethoxyquinazolin-4-yloxy)-1-naphthamido)methyl)nicotinamide

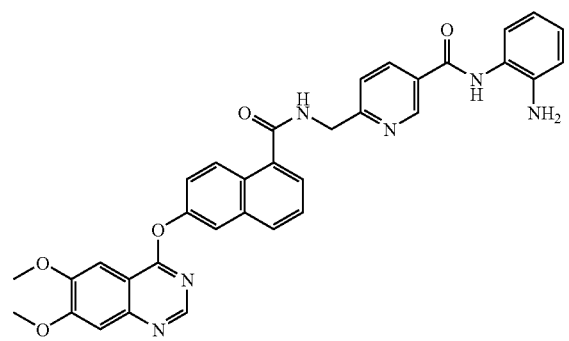

The title compound (41.4 mg, 69% yield) was prepared as a brown solid from 6-(6,7-dimethoxyquinazolin-4-yloxy)-1-naphthoic acid (37.6 mg, 0.1 mmol) and 6-(aminomethyl)-N-(2-aminophenyl)nicotinamide (29.0 mg, 0.12 mmol) by an analogous procedure to that described in example 16. LC-MS (m/z) 601 (M+1).

EXAMPLE 26

Preparation of N-(2-amino-4-fluorophenyl)-6-(2-(6,7-dimethoxyquinazolin-4-yloxy)-1-naphthamido)methyl)nicotinamide

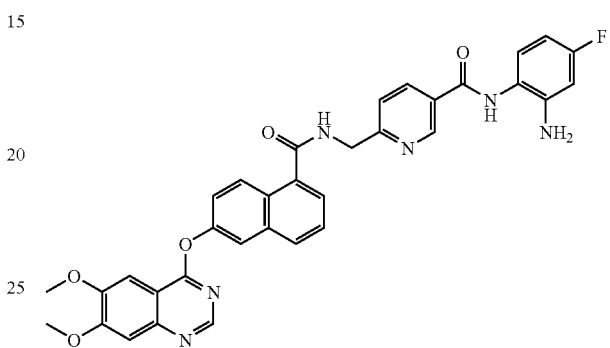

The title compound (43.3 mg, 77% yield) was prepared as a brown solid from 6-(6,7-dimethoxyquinazolin-4-yloxy)-1-naphthoic acid (37.6 mg, 0.1 mmol) and 6-(aminomethyl)-N-(2-amino-4-fluorophenyl)nicotinamide (31.2 mg, 0.12 mmol) by an analogous procedure to that described in example 16. LC-MS (m/z) 619 (M+1).

EXAMPLE 27

Preparation of N-(3-((2-aminophenyl)carbamoyl)benzyl)-6-(6,7-dimethoxyquinazolin-4-yloxy)-1-naphthamide

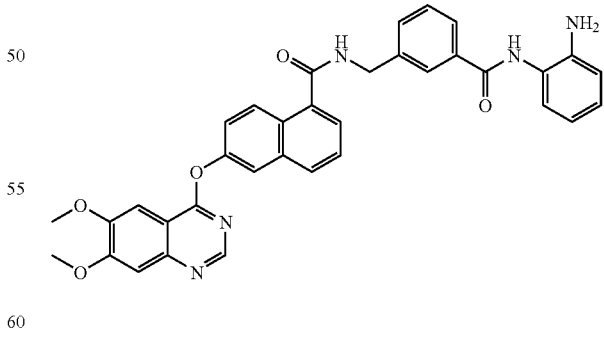

The title compound (48.5 mg, 81% yield) was prepared as a brown solid from 6-(6,7-dimethoxyquinazolin-4-yloxy)-1-naphthoic acid (37.6 mg, 0.1 mmol) and 3-(aminomethyl)-N-(2-aminophenyl)benzamide (28.9 mg, 0.12 mmol) by an analogous procedure to that described in example 16. LC-MS (m/z) 600 (M+1).

EXAMPLE 28

Preparation of N-(4-((2-amino-4-methylphenyl)carbamoyl)benzyl)-6-(6,7-dimethoxyquinazolin-4-yloxy)-1-naphthamide

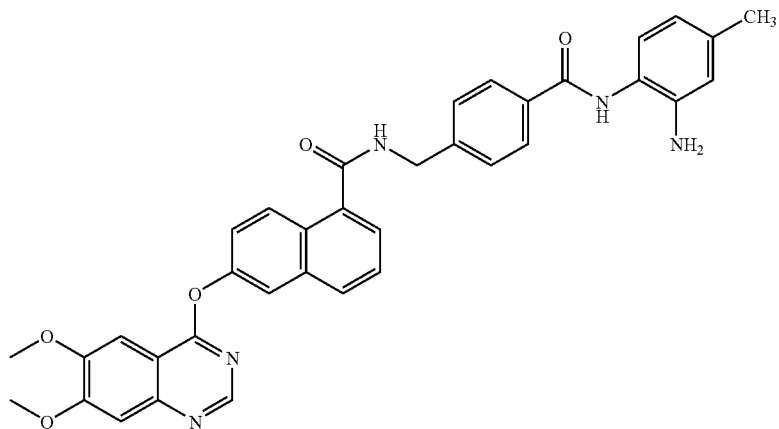

The title compound (52.7 mg, 86% yield) was prepared as a brown solid from 6-(6,7-dimethoxyquinazolin-4-yloxy)-1-naphthoic acid (37.6 mg, 0.1 mmol) and 4-(aminomethyl)-N-(2-amino-4-methylphenyl)benzamide (30.6 mg, 0.12 mmol) by an analogous procedure to that described in example 16. LC-MS (m/z) 614 (M+1).

EXAMPLE 29

Preparation of N-(4-((2-amino-4-methoxyphenyl)carbamoyl)benzyl)-6-(6,7-dimethoxyquinazolin-4-yloxy)-1-naphthamide

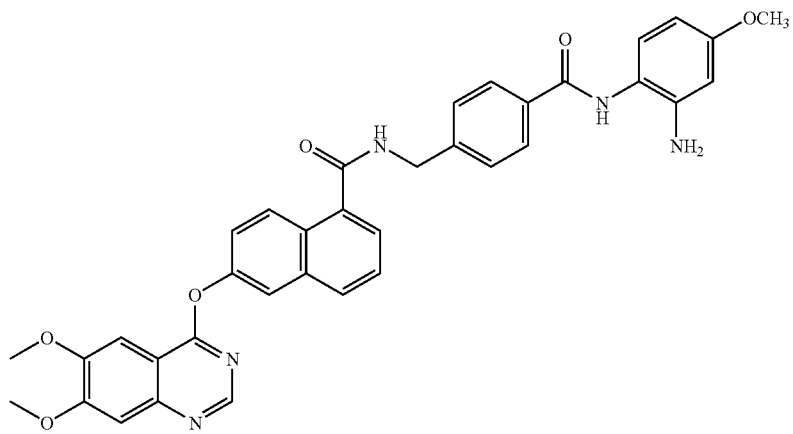

The title compound (51.6 mg, 82% yield) was prepared as a brown solid from 6-(6,7-dimethoxyquinazolin-4-yloxy)-1-naphthoic acid (37.6 mg, 0.1 mmol) and 4-(aminomethyl)-N-(2-amino-4-methoxyphenyl)benzamide (32.5 mg, 0.12 mmol) by an analogous procedure to that described in example 16. LC-MS (m/z) 630 (M+1).

EXAMPLE 30

Preparation of N-(4-((2-amino-4-trifluoromethylphenyl)carbamoyl)benzyl)-6-(6,7-dimethoxyquinazolin-4-yloxy)-1-naphthamide

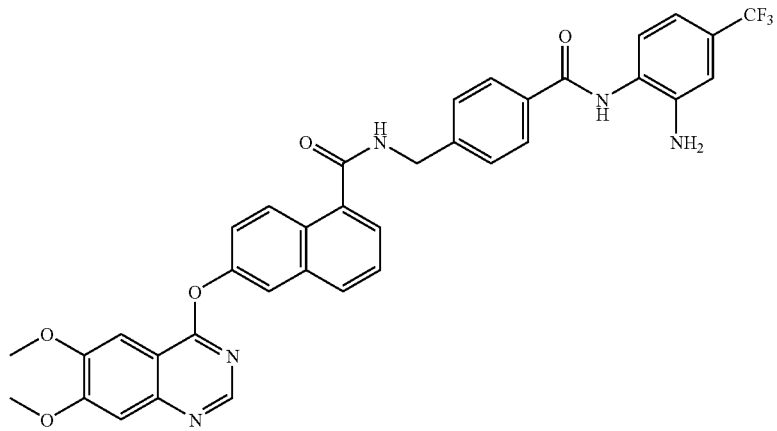

The title compound (46.7 mg, 70% yield) was prepared as a brown solid from 6-(6,7-dimethoxyquinazolin-4-yloxy)-1-naphthoic acid (37.6 mg, 0.1 mmol) and 4-(aminomethyl)-N-(2-amino-4-trifluoromethylphenyl)benzamide (37.1 mg, 0.12 mmol) by an analogous procedure to that described in example 16. LC-MS (m/z) 668 (M+1).

EXAMPLE 31

Preparation of N-(2-aminophenyl)-6-(7-methoxyquinolin-4-yloxy)-1-naphthamide

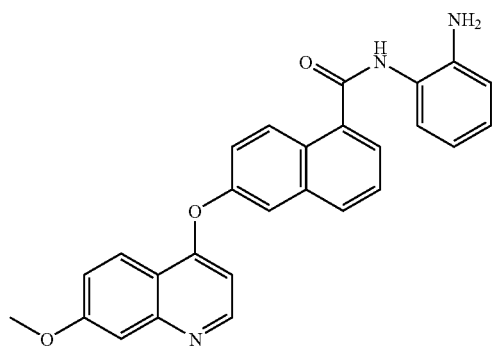

The title compound (39.6 mg, 91% yield) was prepared as a brown solid from 6-(7-methoxyquinolin-4-yloxy)-1-naphthoic acid (34.5 mg, 0.1 mmol) and o-phenylenediamine (43.2 mg, 0.4 mmol) by an analogous procedure to that described in example 16. LC-MS (m/z) $^1$H NMR (DMSO-d$_6$) δ 3.95 (s, 3H, —OCH$_3$), 4.97 (s, 2H, benzene-NH$_2$), 6.60 (d, J=5.2 Hz, 1H, Ar—H), 6.64 (t, J=7.6 Hz, 1H, Ar—H), 6.82 (d, J=7.8 Hz, 1H, Ar—H), 6.99 (t, J=7.4 Hz, 1H, Ar—H), 7.31 (dd, J=2.5 and 9.1 Hz, 1H, Ar—H), 7.38 (d, J=7.6 Hz, 1H, Ar—H), 7.45 (d, J=2.4 Hz, 1H, Ar—H), 7.57 (dd, J=2.4 and 9.2 Hz, 1H, Ar—H), 7.65 (t, J=7.8 Hz, 1H, Ar—H), 7.87-7.88 (m, 2H, Ar—H), 8.07 (d, J=8.2 Hz, 1H, Ar—H), 8.25 (d, J=9.2 Hz, 1H, Ar—H), 8.43 (d, J=9.2 Hz, 1H, Ar—H), 8.65 (d, J=5.2 Hz, 1H, Ar—H), 9.84 (s, 1H, benzene-NH). 436 (M+1).

EXAMPLE 32

Preparation of N-(2-amino-4-fluorophenyl)-6-(7-methoxyquinolin-4-yloxy)-1-naphthamide

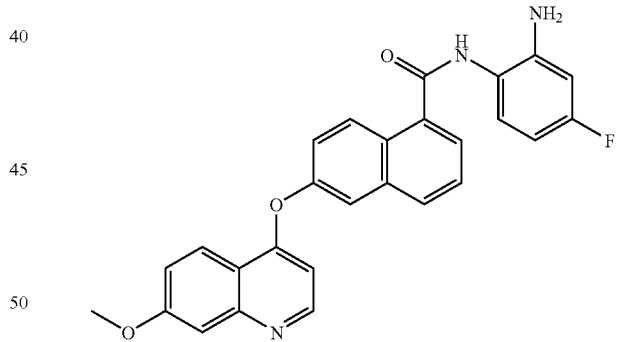

The title compound (33.1 mg, 73% yield) was prepared as a brown solid from 6-(7-methoxyquinolin-4-yloxy)-1-naphthoic acid (34.5 mg, 0.1 mmol) and 4-fluoro-o-phenylenediamine (15.1 mg, 0.12 mmol) by an analogous procedure to that described in example 16. $^1$H NMR (DMSO-d$_6$) δ 3.95 (s, 3H, —OCH$_3$), 5.27 (s, 2H, benzene-NH$_2$), 6.41 (td, J=2.5 and 8.4 Hz, 1H, Ar—H), 6.57-6.61 (m, 2H, Ar—H), 7.30-7.36 (m, 2H, Ar—H), 7.45 (d, J=2.2 Hz, 1H, Ar—H), 7.56 (dd, J=2.2 and 9.2 Hz, 1H, Ar—H), 7.65 (t, J=7.6 Hz, 1H, Ar—H), 7.87-7.91 (m, 2H, Ar—H), 8.07 (d, J=8.3 Hz, 1H, Ar—H), 8.24 (d, J=9.1 Hz, 1H, Ar—H), 8.43 (d, J=9.2 Hz, 1H, Ar—H), 8.65 (d, J=5.1 Hz, 1H, Ar—H), 9.75 (s, 1H, benzene-NH). LC-MS (m/z) 454 (M+1).

EXAMPLE 33

Preparation of N-(4-((2-aminophenyl)carbamoyl)benzyl)-6-(7-methoxyquinolin-4-yloxy)--naphthamide

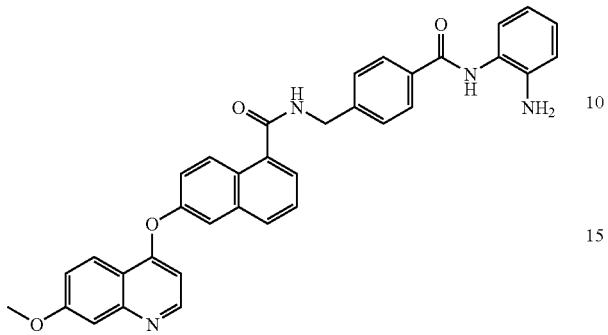

The title compound (48.3 mg, 85% yield) was prepared as a brown solid from 6-(7-methoxyquinolin-4-yloxy)-1-naphthoic acid (34.5 mg, 0.1 mmol) and 4-(aminomethyl)-N-(2-aminophenyl)benzamide (28.9 mg, 0.12 mmol) by an analogous procedure to that described in example 16. $^1$H NMR (DMSO-$d_6$) δ 3.95 (s, 3H, —OCH$_3$), 4.64 (d, J=5.6 Hz, 2H, —CH$_2$), 4.87 (s, 2H, benzene-NH$_2$), 6.58-6.62 (m, 2H, Ar—H), 6.78 (dd, J=1.2 and 7.8 Hz, 1H, Ar—H), 6.97 (td, J=1.4 and 8.1 Hz, 1H, Ar—H), 7.18 (d, J=7.0 Hz, 1H, Ar—H), 7.31 (dd, J=2.5 and 9.2 Hz, 1H, Ar—H), 7.44 (d, J=2.4 Hz, 1H, Ar—H), 7.53-7.56 (m, 3H, Ar—H), 7.62 (t, J=8.0 Hz, 1H, Ar—H), 7.72 (d, J=6.1 Hz, 1H, Ar—H), 7.86 (d, J=2.5 Hz, 1H, Ar—H), 7.98-8.06 (m, 3H, Ar—H), 8.24 (d, J=9.1 Hz, 1H, Ar—H), 8.39 (d, J=9.2 Hz, 1H, Ar—H), 8.64 (d, J=5.2 Hz, 1H, Ar—H), 9.21 (t, J=6.0 Hz, 1H, —CONH), 9.61 (s, 1H, benzene-NH). LC-MS (m/z) 569 (M+1).

EXAMPLE 34

Preparation of N-(2-aminophenyl)-6-(2-(7-methoxyquinolin-4-yloxy)-1-naphthamido)methyl)nicotinamide

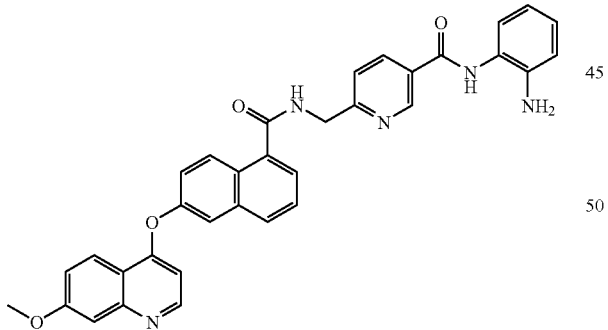

The title compound (46.6 mg, 82% yield) was prepared as a brown solid from 6-(7-methoxyquinolin-4-yloxy)-1-naphthoic acid (34.5 mg, 0.1 mmol) and 6-(aminomethyl)-N-(2-aminophenyl)nicotinamide (29.0 mg, 0.12 mmol) by an analogous procedure to that described in example 16. $^1$H NMR (DMSO-$d_6$) δ 3.95 (s, 3H, —OCH$_3$), 4.74 (s, 2H, —CH$_2$), 4.95 (s, 2H, benzene-NH$_2$), 6.60 (m, 2H, Ar—H), 6.79 (s, 1H, Ar—H), 6.98 (s, 1H, Ar—H), 7.17 (s, 1H, Ar—H), 7.31 (d, J=8.6 Hz, 1H, Ar—H), 7.44 (s, 1H, Ar—H), 7.58-7.63 (m, 3H, Ar—H), 7.77 (s, 1H, Ar—H), 7.87 (s, 1H, Ar—H), 8.05 (d, J=5.6 Hz, 1H, Ar—H), 8.24 (d, J=8.3 Hz, 1H, Ar—H), 8.33 (s, 1H, Ar—H), 8.47 (d, J=7.5 Hz, 1H, Ar—H), 9.13 (s, 1H, Ar—H), 9.25 (s, 1H, —CONH), 9.77 (s, 1H, benzene-NH). LC-MS (m/z) 570 (M+1).

EXAMPLE 35

Preparation of N-(2-aminophenyl)-6-(6,7-dimethoxyquinolin-4-yloxy)-1-naphthamide

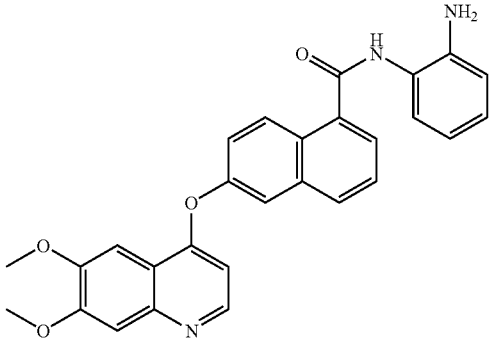

The title compound (40.0 mg, 86% yield) was prepared as a brown solid from 6-(6,7-dimethoxyquinolin-4-yloxy)-1-naphthoic acid (37.5 mg, 0.1 mmol) and o-phenylenediamine (43.2 mg, 0.4 mmol) by an analogous procedure to that described in example 16. $^1$H NMR (DMSO-$d_6$) δ 3.93 (s, 3H, —OCH$_3$), 3.95 (s, 3H, —OCH$_3$), 4.99 (s, 2H, benzene-NH$_2$), 6.56 (d, J=5.2 Hz, 1H, Ar—H), 6.63 (t, J=7.6 Hz, 1H, Ar—H), 6.81 (d, J=7.6 Hz, 1H, Ar—H), 6.98 (t, J=7.2 Hz, 1H, Ar—H), 7.36 (d, J=7.6 Hz, 1H, Ar—H), 7.43 (s, 1H, Ar—H), 7.56-7.58 (m, 2H, Ar—H), 7.65 (t, J=7.6 Hz, 1H, Ar—H), 7.87-7.90 (m, 2H, Ar—H), 8.08 (d, J=8.0 Hz, 1H, Ar—H), 8.43 (d, J=9.2 Hz, 1H, Ar—H), 8.49 (d, J=5.2 Hz, 1H, Ar—H), 9.87 (s, 1H, benzene-NH). LC-MS (m/z) 466 (M+1).

EXAMPLE 36

Preparation of N-(2-amino-4-fluorophenyl)-6-(6,7-dimethoxyquinolin-4-yloxy)-1-naphthamide

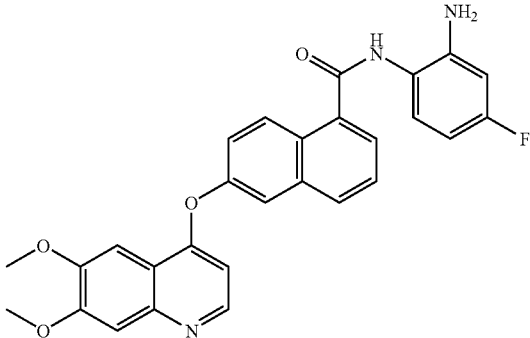

The title compound (39.1 mg, 81% yield) was prepared as a brown solid from 6-(6,7-dimethoxyquinolin-4-yloxy)-1-naphthoic acid (37.5 mg, 0.1 mmol) and 4-fluoro-o-phenylenediamine (15.1 mg, 0.12 mmol) by an analogous procedure to that described in example 16. $^1$H NMR (DMSO-$d_6$) δ 3.93 (s, 3H, —OCH$_3$), 3.95 (s, 3H, —OCH$_3$), 5.31 (s, 2H, benzene-NH$_2$), 6.40 (s, 1H, Ar—H), 6.55-6.59 (m, 2H, Ar—H), 7.30 (d, J=7.6 Hz, 1H, Ar—H), 7.42 (s, 1H, Ar—H), 7.54-7.57 (m, 2H, Ar—H), 7.64 (t, J=8.0 Hz, 1H, Ar—H), 7.89-7.91 (m, 2H, Ar—H), 8.07 (d, J=8.0 Hz, 1H, Ar—H), 8.42 (d, J=9.2 Hz, 1H, Ar—H), 8.49 (d, J=5.2 Hz, 1H, Ar—H), 9.79 (s, 1H, benzene-NH). LC-MS (m/z) 484 (M+1).

EXAMPLE 37

Preparation of N-(4-((2-aminophenyl)carbamoyl)benzyl)-6-(6,7-dimethoxyquinolin-4-yloxy)-1-naphthamide

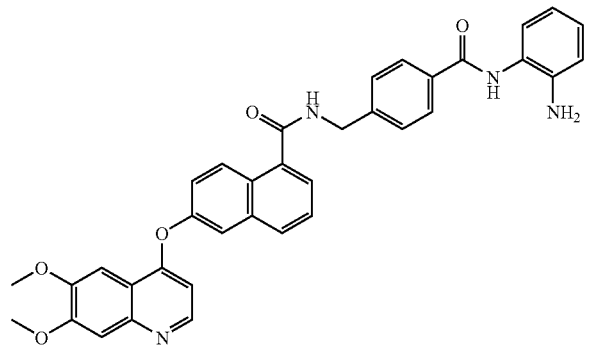

The title compound (49.0 mg, 82% yield) was prepared as a brown solid from 6-(6,7-dimethoxyquinolin-4-yloxy)-1-naphthoic acid (37.5 mg, 0.1 mmol) and 4-(aminomethyl)-N-(2-aminophenyl)benzamide (28.9 mg, 0.12 mmol) by an analogous procedure to that described in example 16. $^1$H NMR (DMSO-d$_6$) δ 3.93 (s, 3H, —OCH$_3$), 3.95 (s, 3H, —OCH$_3$), 4.63 (d, J=5.6 Hz, 2H, —CH$_2$), 4.90 (s, 2H, benzene-NH$_2$), 6.56-6.59 (m, 2H, Ar—H), 6.78 (d, J=7.6 Hz, 1H, Ar—H), 6.96 (t, J=8.1 Hz, 1H, Ar—H), 7.17 (d, J=7.6 Hz, 1H, Ar—H), 7.42 (s, 1H, Ar—H), 7.53-7.55 (m, 4H, Ar—H), 7.62 (t, J=8.0 Hz, 1H, Ar—H), 7.71 (d, J=6.8 Hz, 1H, Ar—H), 7.87 (s, 1H, Ar—H), 7.98-8.06 (m, 3H, Ar—H), 8.39 (d, J=9.2 Hz, 1H, Ar—H), 8.49 (d, J=5.2 Hz, 1H, Ar—H), 9.26 (t, J=6.0 Hz, 1H, —CONH), 9.66 (s, 1H, benzene-NH). LC-MS (m/z) 599 (M+1).

EXAMPLE 38

Preparation of N-(2-aminophenyl)-6-((2-(6,7-dimethoxyquinolin-4-yloxy)-1-naphthamido)methyl)nicotinamide

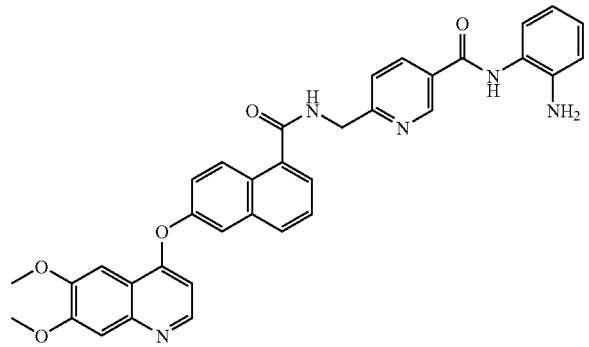

The title compound (47.9 mg, 80% yield) was prepared as a brown solid from 6-(6,7-dimethoxyquinolin-4-yloxy)-1-naphthoic acid (37.5 mg, 0.1 mmol) and 6-(aminomethyl)-N-(2-aminophenyl)nicotinamide (29.0 mg, 0.12 mmol) by an analogous procedure to that described in example 16. $^1$H NMR (DMSO-d$_6$) δ 3.93 (s, 3H, —OCH$_3$), 3.95 (s, 3H, —OCH$_3$), 4.73 (d, J=5.6 Hz, 2H, —CH$_2$), 4.97 (s, 2H, benzene-NH$_2$), 6.57 (m, 2H, Ar—H), 6.77 (d, J=6.4 Hz, 1H, Ar—H), 6.98 (t, J=8.1 Hz, 1H, Ar—H), 7.16 (d, J=5.6 Hz, 1H, Ar—H), 7.42 (s, 1H, Ar—H), 7.55-7.63 (m, 4H, Ar—H), 7.62 (t, J=8.0 Hz, 1H, Ar—H), 7.76 (d, J=6.8 Hz, 1H, Ar—H), 7.88 (s, 1H, Ar—H), 8.06 (s, 1H, Ar—H), 8.33 (s, 1H, Ar—H), 8.45-8.48 (m, 2H, Ar—H), 9.12 (s, 1H, Ar—H), 9.30 (t, J=6.0 Hz, 1H, —CONH), 9.80 (s, 1H, benzene-NH). LC-MS (m/z) 600 (M+1).

EXAMPLE 39

Preparation of N-(2-aminophenyl)-6-(quinolin-4-yloxy)-1-naphthamide

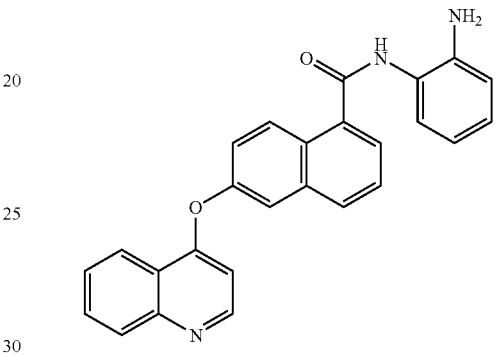

The title compound (35.6 mg, 88% yield) was prepared as a brown solid from 6-(quinolin-4-yloxy)-1-naphthoic acid (31.5 mg, 0.1 mmol) and o-phenylenediamine (43.2 mg, 0.4 mmol) by an analogous procedure to that described in example 16. $^1$H NMR (DMSO-d$_6$) δ 4.97 (s, 2H, benzene-NH$_2$), 6.65 (t, J=7.3 Hz, 1H, Ar—H), 6.75 (d, J=5.1 Hz, 1H, Ar—H), 6.82 (d, J=7.8 Hz, 1H, Ar—H), 7.00 (t, J=7.1 Hz, 1H, Ar—H), 7.38 (d, J=7.5 Hz, 1H, Ar—H), 7.59 (dd, J=2.3 and 9.2 Hz, 1H, Ar—H), 7.64-7.71 (m, 2H, Ar—H), 7.83-7.92 (m, 3H, Ar—H), 8.08 (d, J=8.4 Hz, 2H, Ar—H), 8.37 (d, J=7.9 Hz, 1H, Ar—H), 8.45 (d, J=9.2 Hz, 1H, Ar—H), 8.73 (d, J=5.1 Hz, 1H, Ar—H), 9.85 (s, 1H, benzene-NH). LC-MS (m/z) 406 (M+1).

EXAMPLE 40

Preparation of N-(2-aminophenyl)-6-(8-methylquinolin-4-yloxy)-1-naphthamide

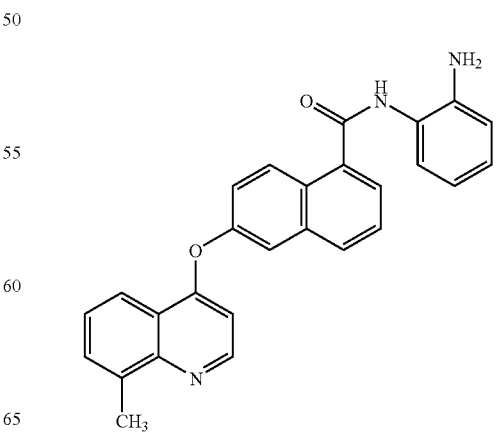

The title compound (37.7 mg, 90% yield) was prepared as a brown solid from 6-(8-methylquinolin-4-yloxy)-1-naphthoic acid (32.9 mg, 0.1 mmol) and o-phenylenediamine (43.2 mg, 0.4 mmol) by an analogous procedure to that described in example 16. $^1$H NMR (DMSO-$d_6$) δ 2.76 (s, 3H, Ar—CH$_3$), 4.97 (s, 2H, benzene-NH$_2$), 6.64 (t, J=7.1 Hz, 1H, Ar—H), 6.78 (d, J=5.0 Hz, 1H, Ar—H), 6.82 (d, J=7.8 Hz, 1H, Ar—H), 6.99 (t, J=7.3 Hz, 1H, Ar—H), 7.38 (d, J=7.5 Hz, 1H, Ar—H), 7.55-7.58 (m, 2H, Ar—H), 7.65 (t, J=7.6 Hz, 1H, Ar—H), 7.71 (d, J=7.0 Hz, 1H, Ar—H), 7.87-7.89 (m, 2H, Ar—H), 8.07 (d, J=8.2 Hz, 1H, Ar—H), 8.20 (d, J=7.9 Hz, 1H, Ar—H), 8.44 (d, J=9.2 Hz, 1H, Ar—H), 8.76 (d, J=5.0 Hz, 1H, Ar—H), 9.84 (s, 1H, benzene-NH). LC-MS (m/z) 420 (M+1).

EXAMPLE 41

Preparation of N-(2-aminophenyl)-6-(7-chloroquinolin-4-yloxy)-1-naphthamide

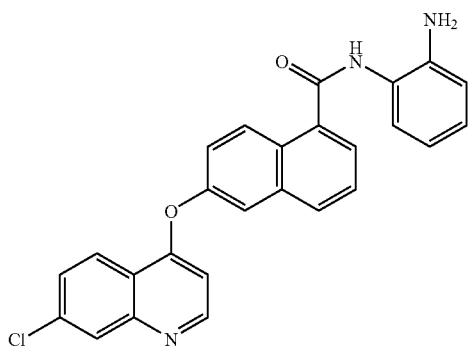

The title compound (33.2 mg, 83% yield) was prepared as a brown solid from 6-(7-chloroquinolin-4-yloxy)-1-naphthoic acid (35.0 mg, 0.1 mmol) and o-phenylenediamine (43.2 mg, 0.4 mmol) by an analogous procedure to that described in example 16. $^1$H NMR (DMSO-$d_6$) δ 4.97 (s, 2H, benzene-NH$_2$), 6.65 (t, J=7.4 Hz, Ar—H), 6.77 (d, J=5.5 Hz, 1H, Ar—H), 6.82 (d, J=7.2 Hz, 1H, Ar—H), 7.00 (t, J=7.0 Hz, 1H, Ar—H), 7.38 (d, J=7.2 Hz, 1H, Ar—H), 7.60 (dd, J=2.6 and 9.2 Hz, 1H, Ar—H), 7.67-7.74 (m, 2H, Ar—H), 7.89 (d, J=7.4 Hz, 1H, Ar—H), 7.94 (d, J=2.4 Hz, 1H, Ar—H), 8.09 (d, J=8.2 Hz, 1H, Ar—H), 8.13 (d, J=2.1 Hz, 1H, Ar—H), 8.41 (d, J=9.0 Hz, 1H, Ar—H), 8.46 (d, J=9.6 Hz, 1H, Ar—H), 8.76 (d, J=5.2 Hz, 1H, Ar—H), 9.85 (s, 1H, benzene-NH). LC-MS (m/z) 440 (M+1).

EXAMPLE 42

Preparation of N-(2-aminophenyl)-6-(8-trifluoromethylquinolin-4-yloxy)-1-naphthamide

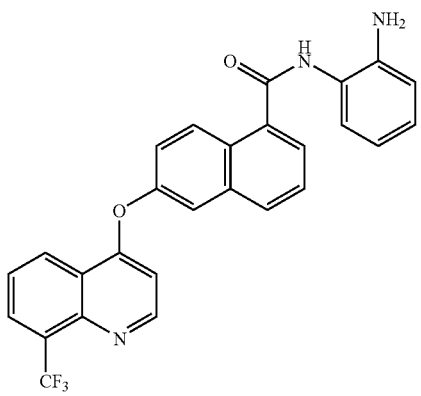

The title compound (38.3 mg, 81% yield) was prepared as a brown solid from 6-(8-trifluoromethylquinolin-4-yloxy)-1-naphthoic acid (39.8 mg, 0.1 mmol) and o-phenylenediamine (43.2 mg, 0.4 mmol) by an analogous procedure to that described in example 16. $^1$H NMR (DMSO-$d_6$) δ 4.98 (s, 2H, benzene-NH$_2$), 6.65 (t, J=7.3 Hz, 1H, Ar—H), 6.83 (d, J=7.6 Hz, 1H, Ar—H), 6.89 (d, J=5.2 Hz, 1H, Ar—H), 7.00 (t, J=7.2 Hz, 1H, Ar—H), 7.38 (d, J=7.5 Hz, 1H, Ar—H), 7.62 (dd, J=2.4 and 9.2 Hz, 1H, Ar—H), 7.68 (t, J=7.7 Hz, 1H, Ar—H), 7.83 (t, J=7.9 Hz, 1H, Ar—H), 7.90 (d, J=7.0 Hz, 1H, Ar—H), 7.97 (d, J=2.3 Hz, 1H, Ar—H), 8.10 (d, J=8.3 Hz, 1H, Ar—H), 8.29 (d, J=7.1 Hz, 1H, Ar—H), 8.47 (d, J=9.2 Hz, 1H, Ar—H), 8.70 (d, J=7.8 Hz, 1H, Ar—H), 8.87 (d, J=5.2 Hz, 1H, Ar—H), 9.86 (s, 1H, benzene-NH). LC-MS (m/z) 474 (M+1).

EXAMPLE 43

Preparation of N-(4-((2-aminophenyl)carbamoyl)benzyl)-6-(7-chloroquinolin-4-yloxy)-1-naphthamide

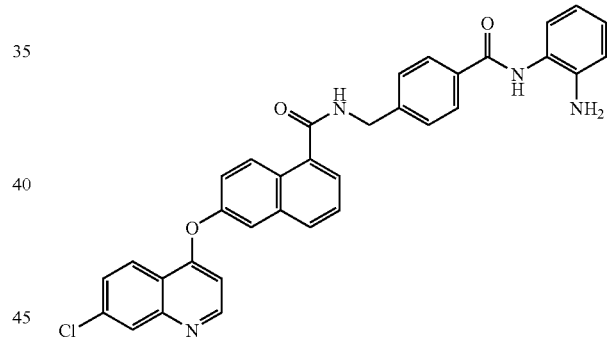

The title compound (42.4 mg, 74% yield) was prepared as a brown solid from 6-(7-chloroquinolin-4-yloxy)-1-naphthoic acid (35.0 mg, 0.1 mmol) and 4-(aminomethyl)-N-(2-aminophenyl)benzamide (28.9 mg, 0.12 mmol) by an analogous procedure to that described in example 16. $^1$H NMR (DMSO-$d_6$) δ 4.64 (d, J=5.8 Hz, 2H, —CH$_2$), 4.87 (s, 2H, benzene-NH$_2$), 6.60 (t, J=7.0 Hz, 1H, Ar—H), 6.75-6.79 (m, 2H, Ar—H), 6.97 (t, J=7.5 Hz, 1H, Ar—H), 7.18 (d, J=7.7 Hz, 1H, Ar—H), 7.53-7.59 (m, 3H, Ar—H), 7.66 (t, J=8.0 Hz, 1H, Ar—H), 7.70-7.74 (m, 2H, Ar—H), 7.92 (d, J=2.0 Hz, 1H, Ar—H), 7.99 (d, J=7.9 Hz, 2H, Ar—H), 8.06 (d, J=8.2 Hz, 1H, Ar—H), 8.13 (s, 1H, Ar—H), 8.39-8.42 (m, 2H, Ar—H), 8.75 (d, J=5.1 Hz, 1H, Ar—H), 9.22 (t, J=5.6 Hz, 1H, —CONH), 9.62 (s, 1H, benzene-NH). LC-MS (m/z) 573 (M+1).

EXAMPLE 44

Preparation of N-(5-(((2-aminophenyl)carbamoyl)pyridin-2-yl)methyl)-6-(8-trifluoromethylquinolin-4-yloxy)-1-naphthamide

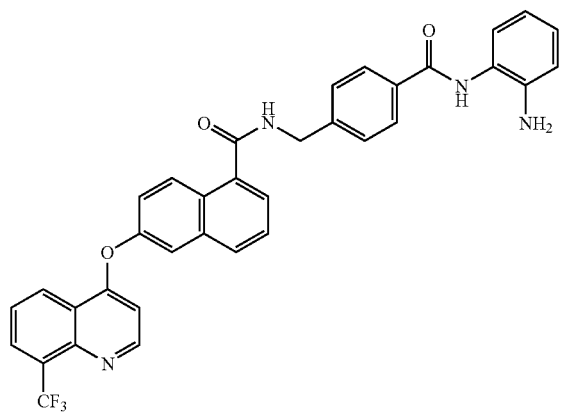

The title compound (47.3 mg, 78% yield) was prepared as a brown solid from 6-(8-trifluoromethylquinolin-4-yloxy)-1-naphthoic acid (38.3 mg, 0.1 mmol) and 6-(aminomethyl)-N-(2-aminophenyl)nicotinamide (29.0 mg, 0.12 mmol) by an analogous procedure to that described in example 16. $^1$H NMR (DMSO-$d_6$) δ 4.64 (d, J=5.6 Hz, 2H, —CH$_2$), 4.87 (s, 2H, benzene-NH$_2$), 6.60 (t, J=7.2 Hz, 1H, Ar—H), 6.78 (d, J=7.8 Hz, 1H, Ar—H), 6.89 (d, J=5.1 Hz, 1H, Ar—H), 6.97 (t, J=7.2 Hz, 1H, Ar—H), 7.18 (d, J=7.9 Hz, 1H, Ar—H), 7.53-7.66 (m, 4H, Ar—H), 7.74 (d, J=6.9 Hz, 1H, Ar—H), 7.83 (t, J=7.9 Hz, 1H, Ar—H), 7.95-8.08 (m, 4H, Ar—H), 8.29 (d, J=7.0 Hz, 1H, Ar—H), 8.42 (d, J=9.1 Hz, 1H, Ar—H), 8.69 (d, J=8.3 Hz, 1H, Ar—H), 8.86 (d, J=5.0 Hz, 1H, Ar—H), 9.22 (t, J=5.5 Hz, 1H, —CONH), 9.61 (s, 1H, benzene-NH). LC-MS (m/z) 607 (M+1).

EXAMPLE 45

Preparation of Tablets

| Tablet formula (1000 tablets): | |
|---|---|
| Compound 31 | 5 g |
| Microcrystalline cellulose | 90 g |
| Sodium carboxymethyl starch | 5 g |
| 4% Polyvidone (K30)/ethanol solution | 50 g |
| Talc powder | 0.5 g |

Compound 31 was sieved through a 100-mesh sieve. Microcrystalline cellulose, sodium carboxymethyl starch and talc powder were sieved through a 80-mesh sieve respectively. Microcrystalline cellulose and sodium carboxymethyl starch were weighed and blended with compound 31 uniformly. 4% Polyvidone (K30)/ethanol solution was added to produce wet granules. The granules were dried and added Talc powder. Then the mixture was mixed and performed tablet compression to obtained tablets.

EXAMPLE 46

Preparation of Capsules

| Capsule formula (1000 tables): | |
|---|---|
| Compound 31 | 5 g |
| Microcrystalline cellulose | 55 g |
| Lactose | 35 g |
| Sodium carboxymethyl starch | 5 g |
| Magnesium stearate | 0.5 g |

Compound 31 was sieved through a 100-mesh sieve. Microcrystalline cellulose, lactose, sodium carboxymethyl starch and magnesium stearate were sieved through a 80-mesh sieve respectively. Microcrystalline cellulose, lactose and sodium carboxymethyl starch were weighed and blended with compound 31 uniformly. Then magnesium stearate was added and mixed. The mixture was performed capsule filling to obtained capsules.

EXAMPLE 47

Preparation of Injection

| Injection formula: | |
|---|---|
| Compound 31 | 1.00 mg |
| DMSO | 0.10 ml |
| Ethanol | 1.00 ml |

Compound 31 was dissolved in DMSO, and then ethanol was added to obtain injection.

EXAMPLE 48

In Vivo Inhibition of Receptor Tyrosine Kinase Activity Via Ligand-Dependent Cell Proliferation Assay by Compounds from Formula (I)

Measurement of In Vivo Inhibition on Receptor Ligand-Dependent Cell Proliferation:

PDGF Dependent Cell Proliferation:

NIH-3T3 mouse fibroblasts cell line engineered to stably express human PDGFIRβ was constructed and used to evaluate PDGF dependent cell proliferation. PDGFRβ NIH-3T3 cells were plated into 96-well plates at 5,000 per well and incubated with serum-free medium for 24 hours. Compounds and PDGF BB (50 ng/ml) were added and incubated for 72 hours in serum-free medium. The effects on proliferation were determined by addition of MTS reagent (Promega) according to the instruction, incubation for 2 hours at 37° C. in CO$_2$ incubator, and record the absorbance at 490 nm using an ELISA plate reader.

VEGF Dependent Cell Proliferation:

HUVEC cells were plated into 96-well plates at 6,000 per well and incubated with serum-free medium for 2 hours.

Compounds and VEGF 165 (50 ng/ml) were added and incubated for 72 hours in serum-free medium. The effects on proliferation were determined by addition of MTS reagent (Promega) according to the instruction, incubation for 2 hours at 37° C. in $CO_2$ incubator, and record the absorbance at 490 nm using an ELISA plate reader.

The experimental results are shown in Table 2.

TABLE 2

| Example (compound) | $GI_{50}$ nM (PDGF ligand-dependent cell proliferation) | $GI_{50}$ nM (VEGF ligand-dependent cell proliferation) |
|---|---|---|
| 16 | 48 | 3 |
| 17 | 40 | 3 |
| 18 | 15 | 7 |
| 19 | 11 | 23 |
| 20 | 23 | 6 |
| 21 | 19 | 5 |
| 22 | 372 | 3 |
| 23 | 148 | 18 |
| 25 | 69 | 13 |
| 31 | 46 | 5 |
| 32 | 20 | 2 |
| 33 | 300 | 8 |
| 34 | 248 | 90 |
| 35 | 5 | 1 |
| 36 | 3 | 2 |
| 37 | 159 | 4 |
| 38 | 74 | 25 |
| 39 | 32 | 107 |
| 40 | 1000 | 1000 |
| 41 | 479 | 105 |
| 42 | 48 | 1000 |
| 43 | 1000 | 288 |
| 44 | 1000 | 1000 |

EXAMPLE 49

In Vitro Inhibition of Total HDAC Enzyme Activity and In Vivo Inhibition of HDAC Subtype Activity by Compounds from Formula (I)

Measurement of In Vitro Inhibition of Total HDAC Enzyme Activity:

The in vitro inhibition of total HDAC enzyme was determined by HDAC Fluorimetric Assay/Drug Discovery Kit (BIOMOL) according to manufacture's instruction.

1. Add Assay buffer, diluted trichostatin A or test inhibitor to appropriate wells of the microtiter plate. Following table lists examples of various assay types and the additions required for each test.

| Sample | Assay Buffer | HeLa Extract (Dilution) | Inhibitor (5x) | Fluor de Lys ™ Substrate (2x) |
|---|---|---|---|---|
| Blank (No Enzyme) | 25 µl | 0 | 0 | 25 µl |
| Control | 10 µl | 15 µl | 0 | 25 µl |
| Trichostatin A | 0 | 15 µl | 10 µl | 25 µl |
| Test Sample | 0 | 15 µl | 10 µl | 25 µl |

2. Add diluted HeLa extract or other HDAC sample to all wells except those that are to be "No Enzyme Controls" (Blank).
3. Allow diluted Fluor de Lys™ Substrate and the samples in the microtiter plate to equilibrate to assay temperature (25° C.).
4. Initiate HDAC reactions by adding diluted substrate (25 µl) to each well and mixing thoroughly.
5. Allow HDAC reactions to proceed for desired length of time and then stop them by addition of Fluor de Lys™ Developer (50 µl). Incubate plate at room temperature (25° C.) for 10-15 min.
6. Read samples in a microtiter-plate reading fluorimeter capable of excitation at a wavelength in the range 350-380 nm and detection of emitted light in the range 440-460 nm.

Measurement of In Vivo Inhibition of HDAC Subtype Activity:

HDAC subtype selectivity inhibition assay of tested compounds was carried out by several reporter gene assays experiments. Briefly, HeLa cells were seeded in 96-well plates the day before transfection to give a confluence of 50-80%. Cells were transfected with one of reporter gene plasmid containing a promoter sequence or response element upstream of a luciferase gene construct using FuGene6 transfection reagent according to the manufacturer's instruction (Roche). The promoters or response elements including p21-promoter was fused upstream to the luciferase gene reporter construct. For normalizing the transfection efficiency, a GFP expression plasmid was cotransfected. Cells were allowed to express protein for 24 hours followed by addition of individual compounds or the vehicle (DMSO). 24 hours later the cells were harvested, and the luciferase assay and GFP assay were performed using corresponding assay kits according to the manufacturer's instructions (Promega).

The experimental results are shown in Table 3.

TABLE 3

| Example (compound) | % inhibition of total HDAC enzyme activity at 30 µM | Class I HDAC (P21 reporter assay) Fold Induction at 10 µM |
|---|---|---|
| CS055 | 50.4 | 33 |
| 16 | 8.6 | 1.3 |
| 17 | 22.5 | 1.1 |
| 18 | 17.1 | 1.1 |
| 19 | 21.9 | 1.4 |
| 20 | 21.9 | 1.5 |
| 21 | 18.6 | 1.1 |
| 22 | 17 | 1.1 |
| 23 | 49.4 | 11.3 |
| 25 | 47.9 | 12.1 |
| 31 | 10.1 | 1.6 |
| 32 | 21.7 | 1.8 |
| 33 | 39.1 | 2.8 |
| 34 | 38.8 | 5.0 |
| 35 | 19.3 | 1.2 |
| 36 | 14.4 | 1.2 |
| 37 | 35.9 | 3.0 |
| 38 | 39.3 | 3.1 |
| 39 | 15.9 | 1.2 |
| 40 | 22.2 | 1.3 |
| 41 | 19.3 | 1.1 |
| 42 | 6.2 | 1.3 |
| 43 | 38.7 | 6.1 |
| 44 | 35.1 | 3.2 |

CS055: Chidamide is a HDACi currently in clinic development against cancers with good efficacy and toxicity profile from Chipscreen Biosciences

EXAMPLE 50

In Vivo Anti-Proliferation by Compounds from Formula (I)

Measurement of In Vivo Cell Proliferation:

Tumor cells were trypsinized and plated into 96-well plates at 3,000 per well and incubated in complete medium with 10% FBS for 24 hours. Compounds were added over a final concentration range of 100 μmol/L to 100 nmol/L in 0.1% DMSO and incubated for 72 hours in complete medium. The effects on proliferation were determined by addition of MTS reagent (Promega) according to the instruction, incubation for 2 hours at 37° C. in $CO_2$ incubator, and record the absorbance at 490 nm using an ELISA plate reader.

Human Cell Lines are Listed Below:
A-498: renal carcinoma
A549: Non small cell lung carcinoma
Bel-7402: Hepatocellular carcinoma
MCF-7: Mammary gland adenocarcinoma
HCT-8: Ileocecal colorectal adenocarcinoma The experimental results are shown in Table 4.

EXAMPLE 51

In Vivo Antitumor Activity of Compound 31 Against Established Human A549 Lung Cancer The antitumor activity of compound 31 was measured in human A549 lung cancer xenograft model. The female nu/nu mice of 14~16 g were fed by normal diet for 3 days. Then the cultured A549 human lung cancer cells were implanted into the armpit of 50 mice. When tumors had reached approximately 6 mm in diameter, the mice were divided into 6 groups randomly. Each group has 8 mice. One group was treated with vehicle. One group was treated with sutent, the positive control drug. The other four groups were treated with compound 31 at doses 5, 10, 20 and 40 mg/kg. Each group was dosed orally once a day for 24 days. Tumor volumes as established by caliper measurements were recorded twice per week, along with body weights. At the end of study, the mice were killed, and tumors were weighed. The tumor growth inhibition of each group was calculated using the formula {[(the average tumor weight of vehicle group)-(the average tumor weight of drug group)]/(the average tumor weight of vehicle group)}×100%. The experimental results are shown in Table 5 and FIG. 1.

TABLE 4

| Example (compound) | $GI_{50}$ μM in A-498 | $GI_{50}$ μM in A549 | $GI_{50}$ μM in Bel-7402 | $GI_{50}$ μM in HCT-8 | $GI_{50}$ μM in MCF-7 |
|---|---|---|---|---|---|
| CS055 | 12.08 | 11.15 | 18.93 | 7.711 | 3.865 |
| 16 | 30.0 | 30.0 | 30.0 | 12.3 | 30.0 |
| 17 | 30.0 | 30.0 | 30.0 | 3.0 | 30.0 |
| 18 | nd | nd | nd | nd | nd |
| 19 | nd | nd | nd | nd | nd |
| 20 | nd | nd | nd | nd | nd |
| 21 | nd | nd | nd | nd | nd |
| 22 | nd | nd | nd | nd | nd |
| 23 | 14.7 | 30.0 | 30.0 | 5.7 | 4.3 |
| 25 | 14.7 | 30.0 | 30.0 | 4.9 | 6.1 |
| 31 | 9.5 | 17.3 | 30.0 | 6.6 | 10.2 |
| 32 | 7.5 | 8.3 | 17.3 | 6.6 | 15.9 |
| 33 | 1.9 | 2.1 | 2.8 | 1.5 | 2.0 |
| 34 | 7.9 | 11.2 | 17.7 | 5.5 | 5.2 |
| 35 | 9.1 | 7.7 | 19.5 | 8.9 | 13.3 |
| 36 | 4.2 | 7.4 | 12.1 | 4.1 | 8.9 |
| 37 | 30.0 | 30.0 | 30.0 | 30.0 | 30.0 |
| 38 | 6.9 | 30.0 | 30.0 | 8.0 | 9.4 |
| 39 | nd | nd | nd | nd | nd |
| 40 | nd | nd | nd | nd | nd |
| 41 | nd | nd | nd | nd | nd |
| 42 | nd | nd | nd | nd | nd |
| 43 | nd | nd | nd | nd | nd |
| 44 | nd | nd | nd | nd | nd | nd*: not determined

CS055: Chidamide is a HDAC inhibitor currently in clinic development against cancers with preference against class I HDAC enzyme

TABLE 5

In vivo antitumor activity of compound 31
against established human A549 lung cancer

| Group [a] | Dose (mg/kg) | Body weight (g) start | Body weight (g) end | Tumor weight (g) | TGI (%) [b] | P |
|---|---|---|---|---|---|---|
| vehicle | — | 20.3 ± 0.9 | 25.4 ± 2.3 | 4.20 ± 0.75 | — | — |
| Sutent | 40 | 20.3 ± 1.4 | 24.4 ± 2.3 | 2.06 ± 0.71 | 50.9 | <0.001 |
| Compound 31 | 40 | 20.0 ± 0.9 | 22.6 ± 2.4 | 1.06 ± 0.54 | 74.8 | <0.001 |
| Compound 31 | 20 | 20.6 ± 1.1 | 24.2 ± 0.7 | 1.50 ± 0.41 | 64.3 | <0.001 |
| Compound 31 | 10 | 19.9 ± 1.3 | 25.1 ± 1.3 | 2.13 ± 0.51 | 49.4 | <0.001 |
| Compound 31 | 5 | 21.1 ± 0.6 | 24.6 ± 1.3 | 2.20 ± 0.57 | 47.6 | <0.001 |

[a] n = 8 animals per group.
[b] Tumor growth inhibition.

EXAMPLE 52

In Vivo Antitumor Activity of Compound 31 Against Established Human HCT-8 Colon Cancer The antitumor activity of compound 31 was measured in human HCT-8 colon cancer xenograft model. The female nu/nu mice of 18~20 g were fed by normal diet for 3 days. Then the cultured HCT-8 human colon cancer cells were implanted into the armpit of 50 mice. When tumors had reached approximately 100 mm$^3$, the mice were divided into 6 groups randomly. Each group has 8 mice. One group was treated with vehicle. One group was treated with sutent, the positive control drug. The other four groups were treated with compound 31 at doses 2.5, 5, 10 and 20 mg/kg. Each group was dosed orally once a day for 20 days. Tumor volumes as established by caliper measurements were recorded twice per week, along with body weights. At the end of study, the mice were killed, and tumors were weighed. The tumor growth inhibition of each group was calculated using the formula {[(the average tumor weight of vehicle group)−(the average tumor weight of drug group)]/(the average tumor weight of vehicle group)}×100%. The experimental results are shown in Table 6 and FIG. 2.

EXAMPLE 53

In Vivo Antitumor Activity of Compound 31 Against Established Human SSMC7721 Liver Cancer The antitumor activity of compound 31 was measured in human SSMC7721 liver cancer xenograft model. The female nu/nu mice of 18~20 g were fed by normal diet for 3 days. Then the cultured SSMC7721 human liver cancer cells were implanted into the armpit of 50 mice. When tumors had reached approximately 100 mm$^3$, the mice were divided into 6 groups randomly. Each group has 8 mice. One group was treated with vehicle. One group was treated with sutent, the positive control drug. The other four groups were treated with compound 31 at doses 2.5, 5, 10 and 20 mg/kg. Each group was dosed orally once a day for 30 days. Tumor volumes as established by caliper measurements were recorded twice per week, along with body weights. At the end of study, the mice were killed, and tumors were weighed. The tumor growth inhibition of each group was calculated using the formula {[(the average tumor weight of vehicle group)−(the average tumor weight of drug group)]/(the average tumor weight of vehicle group)}×100%. The experimental results are shown in Table 7 and FIG. 3.

TABLE 6

In vivo antitumor activity of compound 31 against
established human HCT-8 colon cancer

| Group [a] | Dose (mg/kg) | Body weight (g) start | Body weight (g) end | Tumor weight (g) | TGI (%) [b] | P |
|---|---|---|---|---|---|---|
| vehicle | — | 20.8 ± 1.0 | 22.1 ± 2.1 | 4.78 ± 1.99 | — | — |
| Sutent | 40 | 21.5 ± 0.7 | 22.4 ± 1.1 | 0.23 ± 0.07 | 95.3 | <0.001 |
| Compound 31 | 20 | 20.5 ± 1.3 | 22.5 ± 1.6 | 0.19 ± 0.06 | 96.1 | <0.001 |
| Compound 31 | 10 | 20.7 ± 1.1 | 23.7 ± 0.8 | 0.46 ± 0.15 | 90.3 | <0.001 |
| Compound 31 | 5 | 21.6 ± 1.4 | 24.8 ± 1.5 | 0.78 ± 0.25 | 83.8 | <0.001 |
| Compound 31 | 2.5 | 20.3 ± 0.8 | 24.5 ± 1.1 | 2.18 ± 1.28 | 54.5 | <0.001 |

[a] n = 8 animals per group.
[b] Tumor growth inhibition.

TABLE 7

In vivo antitumor activity of compound 31 against established human SSMC7721 liver cancer

| Group [a] | Dose (mg/kg) | Body weight (g) start | Body weight (g) end | Tumor weight (g) | TGI (%) [b] | P |
|---|---|---|---|---|---|---|
| vehicle | — | 20.8 ± 0.8 | 25.1 ± 1.5 | 4.78 ± 1.99 | — | — |
| Sutent | 40 | 21.0 ± 0.8 | 24.8 ± 1.2 | 1.00 ± 0.68 | 70.3 | <0.001 |
| Compound 31 | 20 | 20.2 ± 1.7 | 21.0 ± 2.2 | 0.53 ± 0.28 | 84.4 | <0.001 |
| Compound 31 | 10 | 20.4 ± 1.6 | 23.6 ± 1.5 | 0.70 ± 0.45 | 79.2 | <0.001 |
| Compound 31 | 5 | 20.8 ± 1.2 | 24.8 ± 1.5 | 1.16 ± 0.55 | 65.4 | <0.001 |
| Compound 31 | 2.5 | 20.1 ± 0.9 | 23.2 ± 2.1 | 1.63 ± 0.70 | 51.7 | <0.001 |

[a] n = 8 animals per group.
[b] Tumor growth inhibition.

EXAMPLE 54

In Vivo Antitumor Activity of Compound 33 and Compound 34 Against Established Human HCT-8 Colon Cancer The antitumor activity of compound 33 and compound 34 were measured in human HCT-8 colon cancer xenograft model. The female nu/nu mice of 18~20 g were fed by normal diet for 3 days. Then the cultured HCT-8 human colon cancer cells were implanted into the armpit of 50 mice. When tumors had reached approximately 100 mm$^3$, the mice were divided into 6 groups randomly. Each group has 8 mice. One group was treated with vehicle. One group was treated with sutent, the positive control drug. Two groups were treated with compound 33. The other two groups were treated with compound 34. Each group was dosed orally once a day for 20 days. Tumor volumes as established by caliper measurements were recorded twice per week, along with body weights. At the end of study, the mice were killed, and tumors were weighed. The tumor growth inhibition of each group was calculated using the formula {[(the average tumor weight of vehicle group)−(the average tumor weight of drug group)]/(the average tumor weight of vehicle group)}×100%. The experimental results are shown in Table 8 and FIG. 4.

EXAMPLE 55

In Vivo Antitumor Activity of Compound 33 and Compound 37 Against Established Human HCT-8 Colon Cancer The antitumor activity of compound 33 and compound 37 were measured in human HCT-8 colon cancer xenograft model. The female nu/nu mice of 18~20 g were fed by normal diet for 3 days. Then the cultured HCT-8 human colon cancer cells were implanted into the armpit of 50 mice. When tumors had reached approximately 100 mm$^3$, the mice were divided into 6 groups randomly. Each group has 8 mice. One group was treated with vehicle. One group was treated with sutent, the positive control drug. Two groups were treated with compound 33. The other two groups were treated with compound 37. Compound 33 was administered twice a day with an interval of 6 hours. Other drugs and vehicle were administered once a day. Each group was dosed orally for 20 days. Tumor volumes as established by caliper measurements were recorded twice per week, along with body weights. At the end of study, the mice were killed, and tumors were weighed. The tumor growth inhibition of each group was calculated using the formula {[(the average tumor weight of vehicle group)−(the average tumor weight of drug group)]/(the average tumor weight of vehicle group)}×100%. The experimental results are shown in Table 9 and FIG. 5.

TABLE 8

In vivo antitumor activity of compound 33 and compound 34 against established human HCT-8 colon cancer

| Group [a] | Dose (mg/kg) | Body weight (g) start | Body weight (g) end | Tumor weight (g) | TGI (%) [b] | P |
|---|---|---|---|---|---|---|
| vehicle | — | 19.4 ± 1.6 | 21.2 ± 2.4 | 4.08 ± 0.95 | — | — |
| Sutent | 40 | 20.6 ± 1.2 | 22.1 ± 1.5 | 0.44 ± 0.15 | 89.1 | <0.001 |
| Compound 33 | 60 | 19.4 ± 0.8 | 21.4 ± 1.5 | 1.98 ± 0.61 | 51.5 | <0.001 |
| Compound 33 | 30 | 19.0 ± 1.3 | 21.1 ± 2.2 | 2.31 ± 0.43 | 43.3 | <0.001 |
| Compound 34 | 60 | 19.6 ± 1.1 | 21.6 ± 2.3 | 2.74 ± 0.77 | 32.7 | <0.001 |
| Compound 34 | 30 | 19.7 ± 1.2 | 21.2 ± 1.9 | 3.95 ± 0.73 | 3.07 | >0.05 |

[a] n = 8 animals per group.
[b] Tumor growth inhibition.

TABLE 9

In vivo antitumor activity of compound 33 and compound 37 against established human HCT-8 colon cancer

| Group [a] | Dose (mg/kg) | Body weight (g) start | Body weight (g) end | Tumor weight (g) | TGI (%) [b] | P |
|---|---|---|---|---|---|---|
| vehicle | — | 21.1 ± 0.7 | 23.4 ± 1.5 | 6.13 ± 0.28 | — | — |
| Sutent | 40 | 21.3 ± 0.6 | 23.7 ± 0.8 | 0.29 ± 0.08 | 95.3 | <0.001 |
| Compound 33 | 60 × 2 | 20.1 ± 0.9 | 19.0 ± 1.8 | 0.45 ± 0.05 | 92.6 | <0.001 |
| Compound 33 | 30 × 2 | 21.1 ± 1.2 | 22.6 ± 1.6 | 0.73 ± 0.36 | 88.1 | <0.001 |
| Compound 37 | 60 | 20.8 ± 0.8 | 24.1 ± 2.1 | 3.36 ± 0.80 | 45.1 | <0.001 |
| Compound 37 | 30 | 20.6 ± 0.8 | 23.6 ± 2.2 | 3.89 ± 1.19 | 36.5 | <0.001 |

[a] n = 8 animals per group.
[b] Tumor growth inhibition.

EXAMPLE 56

In Vivo Antitumor Activity of Compound 33 and Compound 37 Against Established Human SSMC7721 Liver Cancer The antitumor activity of compound 33 and compound 37 were measured in human SSMC7721 liver cancer xenograft model. The female nu/nu mice of 18~20 g were fed by normal diet for 3 days. Then the cultured SSMC7721 human liver cancer cells were implanted into the armpit of 50 mice. When tumors had reached approximately 100 mm$^3$, the mice were divided into 6 groups randomly. Each group has 8 mice. One group was treated with vehicle. One group was treated with sutent, the positive control drug. Two groups were treated with compound 33. The other two groups were treated with compound 37. Each group was dosed orally once a day for 30 days. Tumor volumes as established by caliper measurements were recorded twice per week, along with body weights. At the end of study, the mice were killed, and tumors were weighed. The tumor growth inhibition of each group was calculated using the formula {[(the average tumor weight of vehicle group)–(the average tumor weight of drug group)]/(the average tumor weight of vehicle group)}×100%. The experimental results are shown in Table 10 and FIG. 6.

TABLE 10

In vivo antitumor activity of compound 33 and compound 37 against established human SSMC7721 liver cancer

| Group [a] | Dose (mg/kg) | Body weight (g) start | Body weight (g) end | Tumor weight (g) | TGI (%) [b] | P |
|---|---|---|---|---|---|---|
| vehicle | — | 21.1 ± 0.4 | 24.5 ± 1.6 | 2.25 ± 0.85 | — | — |
| Sutent | 40 | 21.2 ± 1.1 | 24.0 ± 0.6 | 0.88 ± 0.39 | 61.1 | <0.001 |
| Compound 33 | 60 | 21.4 ± 1.3 | 25.4 ± 2.8 | 1.48 ± 0.89 | 34.4 | >0.05 |
| Compound 33 | 30 | 20.8 ± 0.5 | 24.0 ± 1.7 | 1.63 ± 0.47 | 27.8 | >0.05 |
| Compound 37 | 60 | 21.4 ± 0.6 | 24.3 ± 1.1 | 1.28 ± 0.51 | 43.3 | <0.05 |
| Compound 37 | 30 | 20.7 ± 1.2 | 25.3 ± 0.9 | 1.45 ± 0.58 | 35.6 | <0.05 |

[a] n = 8 animals per group.
[b] Tumor growth inhibition.

What is claimed is:

1. An isolated compound of formula I:

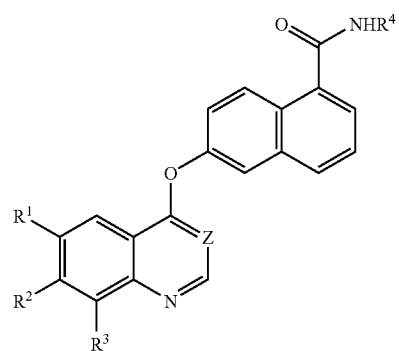

(I)

or its stereoisomer, enantiomer, diastereomer, or a pharmaceutically acceptable salt thereof, wherein Z is CH or N;

$R^1$, $R^2$ and $R^3$ are independently hydrogen, halo, alkyl, alkoxy or trifluoromethyl;

R⁴ is

[structure: aminophenyl group with R⁵ substituent], or [structure: -X-C(=O)-NH-aminophenyl with R⁵];

X is a benzene ring or a pyridine ring;
R⁵ is one or more substituents selected from hydrogen, halo, alkyl, alkoxy or trifluoromethyl.

2. A compound of claim 1, wherein
Z is CH;
R¹, R² and R³ are independently hydrogen, halo, alkyl, alkoxy or trifluoromethyl;
R⁴ is

[structure: aminophenyl group with R⁵], or [structure: -X-C(=O)-NH-aminophenyl with R⁵];

X is a benzene ring or a pyridine ring;
R⁵ is one or more substituents selected from hydrogen, halo, alkyl, alkoxy or trifluoromethyl.

3. A compound of claim 1, wherein
Z is CH;
R¹, R² and R³ are independently hydrogen or alkoxy;
R⁴ is

[structure: aminophenyl group with R⁵], or [structure: -X-C(=O)-NH-aminophenyl with R⁵];

X is a benzene ring or a pyridine ring;
R⁵ is one or more substituents selected from hydrogen, halo, alkyl, alkoxy or trifluoromethyl.

4. A compound of claim 1, wherein
Z is CH;
R¹ and R² are independently hydrogen or methoxy;
R³ is H;
R⁴ is

[structure: aminophenyl group with R⁵], or [structure: -X-C(=O)-NH-aminophenyl with R⁵];

X is a benzene ring or a pyridine ring;
R⁵ is one or more substituents selected from hydrogen, halo, alkyl, alkoxy or trifluoromethyl.

5. A compound of claim 1, wherein
Z is CH;
R¹ and R² are independently hydrogen or methoxy;
R³ is H;
R⁴ is

[structure: aminophenyl group with R⁵], or [structure: -X-C(=O)-NH-aminophenyl with R⁵];

X is a benzene ring or a pyridine ring;
R⁵ is H or F.

6. A method for the preparation of a compound of formula I $$\text{(I)}$$

[structure of formula (I): naphthalene-1-carboxamide (C(=O)NHR⁴) with 6-oxy linkage to quinazoline bearing R¹, R², R³ substituents and Z position]

wherein
Z is CH or N;
R¹, R² and R³ are independently hydrogen, halo, alkyl, alkoxy or trifluoromethyl;
R⁴ is

[structure: aminophenyl group with R⁵], or [structure: -X-C(=O)-NH-aminophenyl with R⁵];

X is a benzene ring or a pyridine ring;
R⁵ is one or more substituents selected from hydrogen, halo, alkyl, alkoxy or trifluoromethyl;
a stereoisomer, enantiomer, diastereomer, or pharmaceutically acceptable salts thereof comprising reacting a compound of formula (II)

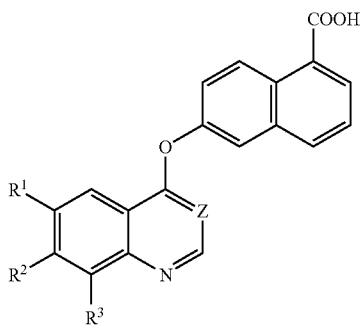

with a compound of formula (III)

in the presence of an organic solvent and a peptide condensing agent, to form compound (I), wherein $R^1$, $R^2$, $R^3$, $R^4$ and Z are as defined above.

7. The method of claim 6, wherein said peptide condensing agent is 1-Ethyl-3-(3-dimethyl-aminopropyl)carbodiimide, dicyclohexylcarbodiimide or N,N'-carbonyldiimidazole.

8. The method of claim 6, wherein said organic solvent is benzene, toluene, tetrahydrofuran, dioxane, dichloromethane, chloroform or N,N-dimethylformamide.

9. A pharmaceutical composition comprising an effective amount of a compound according to claim 1 and at least one pharmaceutically acceptable excipient, carrier or diluent.

10. A pharmaceutical composition as claimed in claim 9, in the form of a tablet, capsule, powder, syrup, solution or suspension.

11. A dosage form unit of the pharmaceutical composition of claim 9 comprising an amount within the range of about 0.0001 to about 200 mg of said compound.

12. A dosage form unit of the pharmaceutical composition of claim 11 comprising an amount within the range of about 0.1 to about 100 mg of said compound.

13. A dosage form unit of the pharmaceutical composition of claim 12 comprising an amount within the range of about 1 to about 100 mg of said compound.

14. A dosage form unit of the pharmaceutical composition of claim 13 comprising an amount within the range of about 5 to about 80 mg of said compound.

15. A dosage form unit of the pharmaceutical composition of claim 14 comprising an amount within the range of about 10 to about 75 mg of said compound.

16. A dosage form unit of the pharmaceutical composition of claim 15 comprising an amount within the range of about 20 to about 75 mg of said compound.

17. A dosage form unit of the pharmaceutical composition of claim 16 comprising an amount within the range of about 25 to about 75 mg of said compound.

18. A dosage form unit of the pharmaceutical composition of claim 13 comprising an amount within the range of about 25 to about 100 mg of said compound.

* * * * *